US012667306B2

(12) United States Patent
Zenisek

(10) Patent No.: US 12,667,306 B2
(45) Date of Patent: Jun. 30, 2026

(54) MEDICATION MONITORING BASED ON LOCAL FIELD POTENTIAL

(71) Applicant: Medtronic, Inc., Minneapolis, MN (US)

(72) Inventor: Todd D. Zenisek, Georgetown, TX (US)

(73) Assignee: Medtronic, Inc., Minneapolis, MN (US)

( * ) Notice: Subject to any disclaimer, the term of this patent is extended or adjusted under 35 U.S.C. 154(b) by 942 days.

(21) Appl. No.: 17/811,001

(22) Filed: Jul. 6, 2022

(65) Prior Publication Data

US 2023/0012100 A1 Jan. 12, 2023

Related U.S. Application Data

(60) Provisional application No. 63/219,300, filed on Jul. 7, 2021.

(51) Int. Cl.
*A61B 5/00* (2006.01)
*A61B 5/388* (2021.01)

(52) U.S. Cl.
CPC ............ *A61B 5/4848* (2013.01); *A61B 5/388* (2021.01); *A61B 5/4833* (2013.01); *A61B 5/4842* (2013.01)

(58) Field of Classification Search
None
See application file for complete search history.

(56) References Cited

U.S. PATENT DOCUMENTS 8,190,251 B2    5/2012  Molnar et al.
8,849,392 B2    9/2014  Lozano 10,016,606 B2    7/2018  Afshar et al.
10,596,379 B2    3/2020  Arlotti et al.
10,849,525 B2   12/2020  Parker et al.
2005/0113744 A1    5/2005  Donoghue et al.
2014/0213926 A1    7/2014  Vaidyanathan
2014/0358024 A1   12/2014  Nelson et al.
2015/0202447 A1*    7/2015  Afshar .............. A61N 1/36171
                                                                    600/378
2017/0056642 A1*    3/2017  Moffitt ................. A61N 1/3605
(Continued)

FOREIGN PATENT DOCUMENTS

WO      WO-2020239742 A1 * 12/2020    ........... A61B 5/7267
WO          2021022332 A1    2/2021

OTHER PUBLICATIONS

Giannicola et al., "The Effects of Levodopa and Deep Brain Stimulation on Subthalamic Local Field Low-Frequency Oscillations in Parkinson's Disease", Neurosignals, vol. 21, Apr. 26, 2012, p. 89-98.

(Continued)

*Primary Examiner* — Jacqueline Cheng
*Assistant Examiner* — Jairo H Portillo
(74) *Attorney, Agent, or Firm* — Shumaker & Sieffert, P.A.

(57)                    ABSTRACT

A method for determining an efficacy of medication treatment for a patient includes determining, by one or more processors, based on a local field potential (LFP) activity of the patient, when the patient takes medication and/or a duration of when the medication is effective. The method further includes outputting, by the one or more processors, an indication of when the patient takes the medication and/or the duration of when the medication is effective to facilitate a treatment for the patient.

18 Claims, 14 Drawing Sheets

(56) References Cited

U.S. PATENT DOCUMENTS

2021/0196175 A1 *   7/2021   Levy ..................... A61B 5/7267
2021/0251525 A1      8/2021   Probst et al.

OTHER PUBLICATIONS

Thompson et al., "Clinical Implications of Local Field Potentials for Understanding and Treating Movement Disorders", Stereotact Funct Neurosurg, Aug. 27, 2014, p. 251-263.
Tinkhauser et al., "Beta burst dynamics in Parkinson's disease OFF and ON dopaminergic medication", Brain, vol. 140, Oct. 10, 2017, p. 2968-2981.

* cited by examiner

100

114B
114A
118
116
120
122

PROGRAMMER
104

112

110

108

IMD
106

104

DETERMINE, BASED ON LFP ACTIVITY OF PATIENT, WHEN PATIENT TAKES MEDICATION ⟋1302

DETERMINE, BASED ON LFP ACTIVITY OF PATIENT, A DURATION OF WHEN MEDICATION IS EFFECTIVE FOR TREATMENT OF PATIENT ⟋1304

OUTPUT INDICATION OF WHEN PATIENT TAKES MEDICATION AND/OR DURATION OF WHEN MEDICATION IS EFFECTIVE FOR TREATMENT OF PATIENT ⟋1306

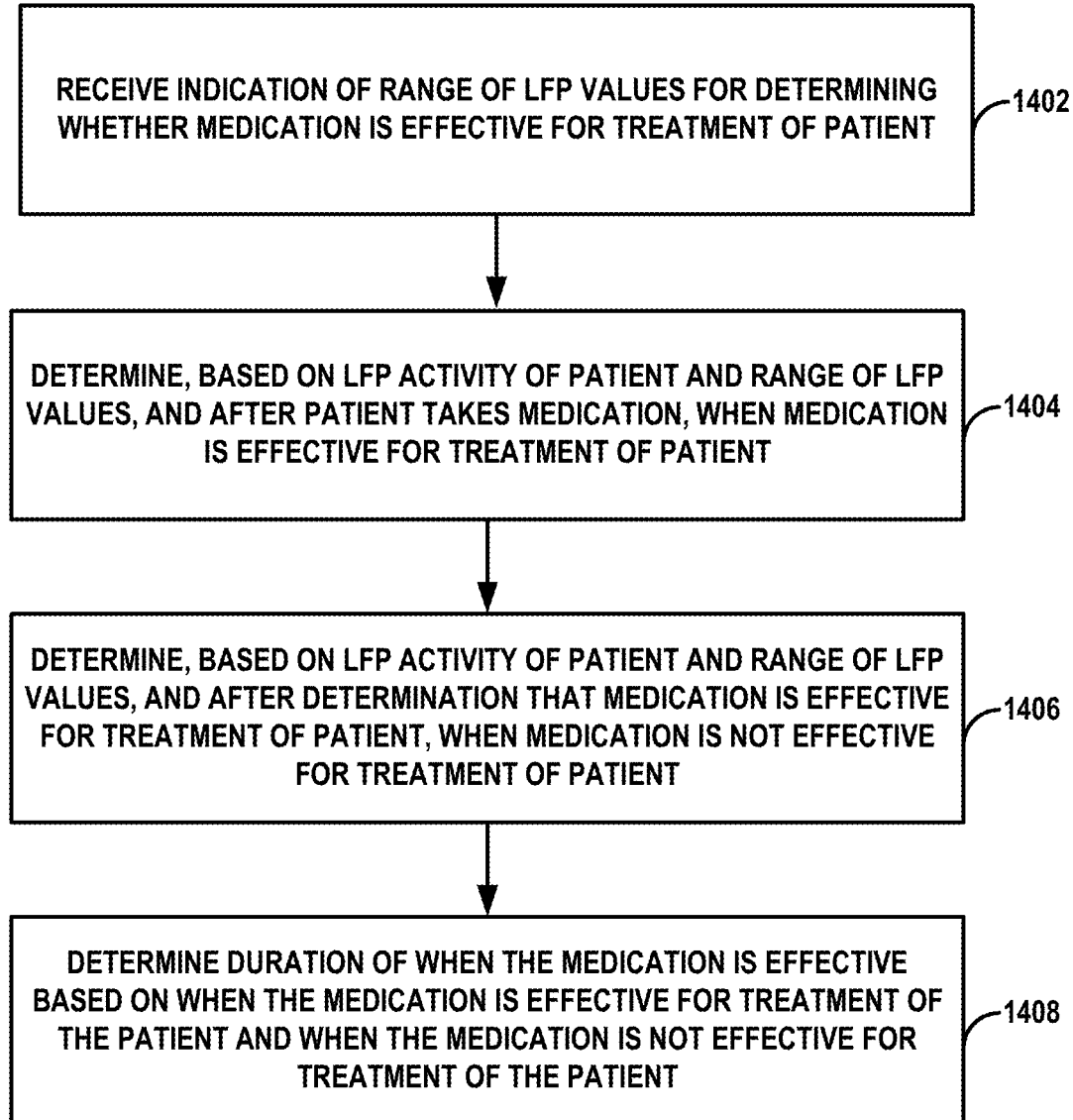

RECEIVE INDICATION OF RANGE OF LFP VALUES FOR DETERMINING WHETHER MEDICATION IS EFFECTIVE FOR TREATMENT OF PATIENT ⌐1402

DETERMINE, BASED ON LFP ACTIVITY OF PATIENT AND RANGE OF LFP VALUES, AND AFTER PATIENT TAKES MEDICATION, WHEN MEDICATION IS EFFECTIVE FOR TREATMENT OF PATIENT ⌐1404

DETERMINE, BASED ON LFP ACTIVITY OF PATIENT AND RANGE OF LFP VALUES, AND AFTER DETERMINATION THAT MEDICATION IS EFFECTIVE FOR TREATMENT OF PATIENT, WHEN MEDICATION IS NOT EFFECTIVE FOR TREATMENT OF PATIENT ⌐1406

DETERMINE DURATION OF WHEN THE MEDICATION IS EFFECTIVE BASED ON WHEN THE MEDICATION IS EFFECTIVE FOR TREATMENT OF THE PATIENT AND WHEN THE MEDICATION IS NOT EFFECTIVE FOR TREATMENT OF THE PATIENT ⌐1408

FIG. 14

MEDICATION MONITORING BASED ON LOCAL FIELD POTENTIAL

This application claims the benefit of U.S. Provisional Patent Application No. 63/219,300, filed 7 Jul. 2021, the entire contents of which is incorporated herein by reference.

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device delivers electrical stimulation therapy via one or more leads that include electrodes located proximate to target locations associated with the brain, the spinal cord, pelvic nerves, peripheral nerves, or the gastrointestinal tract of a patient. For bipolar stimulation, the electrodes used for stimulation may be on one or more leads. For unipolar stimulation, the electrodes may be on one or more leads, and an electrode on a stimulator housing located remotely from the target site (e.g., near clavicle). It may be possible to use leadless stimulation using electrodes mounted on the stimulation housing. Hence, electrical stimulation is used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current pulse amplitude, a pulse width, and a pulse frequency as stimulation parameters. A set of parameters, such as a set including electrode combination, electrode polarity, amplitude, pulse width, and pulse rate, may be referred to as a program in the sense that they define the electrical stimulation therapy to be delivered to the patient.

SUMMARY

This disclosure describes example techniques for using local field potential (LFP) activity to monitor medication supplementation, onset/duration, effectiveness, etc. to assist the Healthcare professionals (HCPs) to understand how compliant the patient is and the medication's effectiveness. A medical device may monitor disease progression in Parkinson's Disease (PD) patients, as one example, through LFP and medication supplementation. In this way, the medical device may with a practical application of providing more accurate patient information as related to patient compliance and medication effectiveness (as two examples) for the HCP when treating their patients.

In this way, a system may help the HCP to understand a number of doses the patient takes. In some examples, the system may be configured monitor the dosing by the HCP denoting within the system, at what times the dosing should occur, and may look for the medication and/or LFP reaction that would indicate the medication was taken and/or if the medication/LFP reaction does not occur, remind the patient to take their medication). The system may be configured to identify one or more of an onset of when the medication should have therapeutic effect via LFP or another technique, a duration of action via LFP or another technique, or a loss of therapeutic effect via LFP or another technique. The system may be configured to identify extra, or missed, doses and report that back to the HCP via in the either the reports or other timeline reporting system. This data could also be sent to an HCP monitoring site that might alert the HCP if there is a trend of extra or missed doses. If missed doses are identified, the system may be configured to remind the patient to take their medication via an alert system such as alert from the medical device and/or patient programmer. The system may be configured to help determine if the efficacy of the stimulation and/or medication has changed over time possibly due to various issues such as, for example, dementia, forgetfulness, and disease progression. The system may be configured to reduce stimulation based on the efficacy of the drug when at peak, or other defined efficacy, determined by the system logic/algorithm.

In one example, this disclosure describes a method for determining an efficacy of medication treatment for a patient including determining, by one or more processors, based on a local field potential (LFP) activity of the patient, when the patient takes medication and/or a duration of when the medication is effective and outputting, by the one or more processors, an indication of when the patient takes the medication and/or the duration of when the medication is effective to facilitate a treatment for the patient.

In another example, this disclosure describes a system for providing stimulation to a patient including sensing circuitry configured to generate a LFP activity of a patient and processing circuitry configured to determine, based on the LFP activity of the patient, when the patient takes medication and/or a duration of when the medication is effective and output an indication of when the patient takes the medication and/or the duration of when the medication is effective to facilitate a treatment for the patient.

In one example, this disclosure describes computer-readable storage medium having stored thereon instructions that, when executed, cause processing circuitry to determine, based on a LFP activity of the patient, when the patient takes medication and/or a duration of when the medication is effective and output an indication of when the patient takes the medication and/or the duration of when the medication is effective to facilitate a treatment for the patient.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIG. 14 is a flowchart illustrating an example operation for determining the duration of when the medication is effective for treatment of the patient based on a range of LFP values in accordance with techniques of the disclosure.

DETAILED DESCRIPTION

Figure 1:
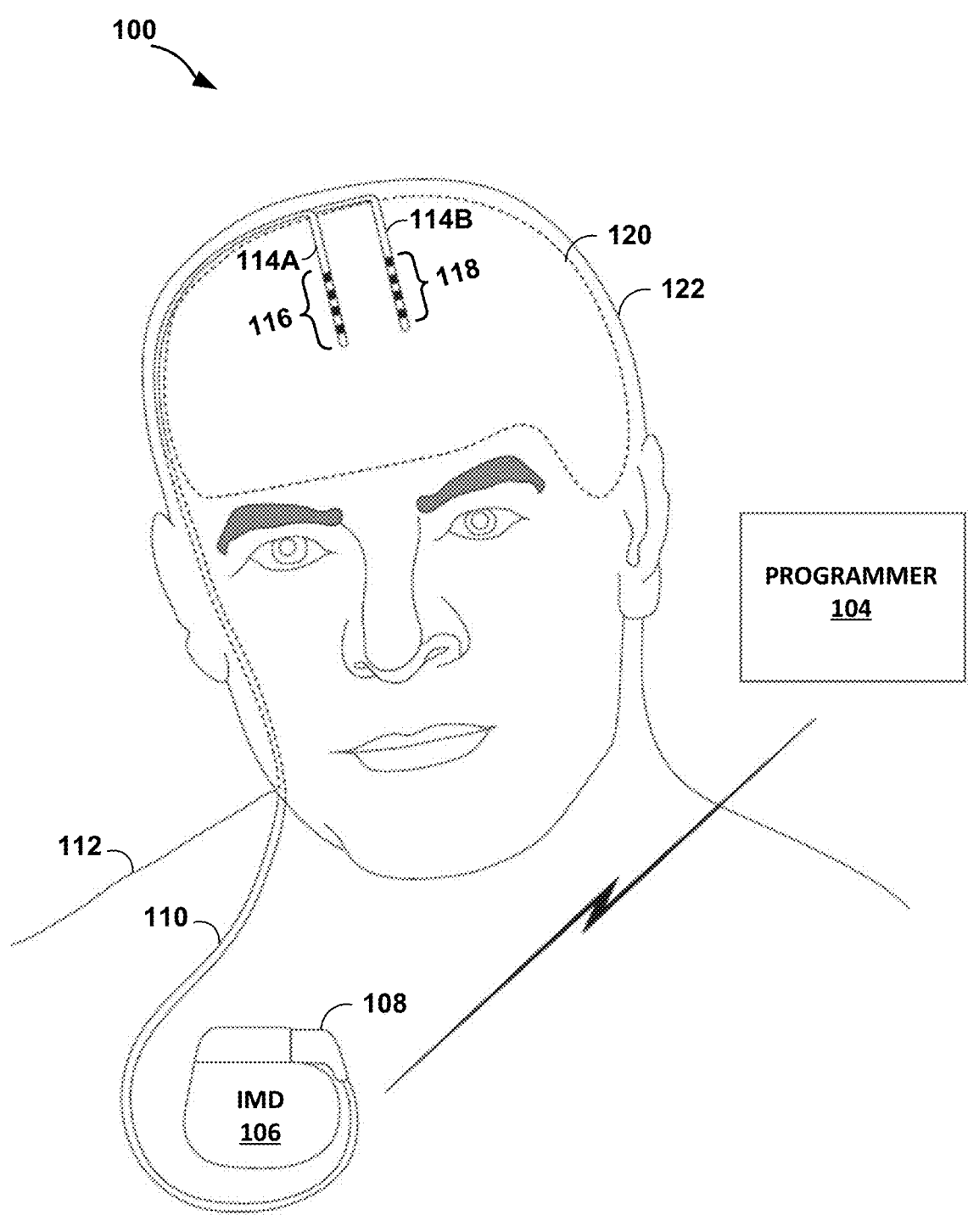
FIG. 1 is a conceptual diagram illustrating an example system that includes an implantable medical device (IMD) configured to deliver electrical stimulation to a patient according to an example of the techniques of the disclosure.

This disclosure describes example techniques for systems directed to electrical stimulation therapy (e.g., neuromodulation such as deep brain stimulation (DBS) therapy). Electrical stimulation therapy may be delivered via multiple electrodes of one or more leads (e.g., cylindrical or paddle leads) implanted in the brain of a patient. Electrical stimulation therapy may be adaptively adjusted for a patient using a set of programs. For example, sensing circuitry may sense one or more bioelectric signals of a brain of a patient and stimulation generation circuitry may generate the electrical stimulation based on the one or more bioelectric signals and the set of programs.

Healthcare professionals (HCPs) may not have information to directly understand how well a medication works for a patient receiving electrical stimulation therapy. For example, the HCP may not have access to information relating to how regularly the patient takes the medication or how long the medication is effective.

While examples herein refer to a patient receiving electrical stimulation therapy, in some examples, techniques described herein or determining an efficacy of medication treatment may apply to patients that do not receive electrical stimulation therapy. For instance, leads may be implanted in a patient simply for sensing and determining when the patient is taking medication and whether the medication is effective, but never provide any electrical stimulation. That is, in some examples, therapy may be provided by medication without electrical stimulation and implantable circuitry may sense to improve the therapy provided outside of the implantable circuitry (e.g., medication). In some other examples, the medical device may provide stimulation to supplement the therapy from the medication, and/or may provide stimulation to treat one disorder, and the medication treats another disorder.

This disclosure generally relates to a process for using local field potential (LFP) activity to monitor medication supplementation, onset/duration, effectiveness, etc. to assist the HCP to understand one or more of how compliant the patient is, the medication's effectiveness, or a potential disease state progression. As described further herein, techniques may monitor one or more of medication supplementation, onset/duration, or effectiveness based on one or more bioelectric signals (e.g., a LFP activity) measured by sensing circuitry of a medical device (e.g., a medical device configured to provide electrical stimulation therapy using the one or more bioelectric signals). In this way, a medical device may provide medication information without relying on an additional device or additional circuitry of the medical device. In some examples, however, a medical device may generate an indication of the LFP activity at a brain of a patient without applying electrical stimulation to the brain of the patient.

In some examples, a medical device may monitor disease progression in peritoneal dialysis (PD) patients, as one example, through LFP and medication supplementation. In this way, the medical device may provide a better picture for the HCP when treating their patients.

FIG. 1 is a conceptual diagram illustrating an example system 100 that includes an implantable medical device (IMD) 106 configured to deliver adaptive deep brain stimulation (DBS) to a patient 112. DBS may be adaptive in the sense that IMD 106 may adjust, increase, or decrease the magnitude of one or more parameters of the DBS in response to changes in patient activity or movement, a severity of one or more symptoms of a disease of the patient, a presence of one or more side effects due to the DBS, or one or more sensed signals of the patient.

For instance, one example of system 100 is a bi-directional DBS system with capabilities to both deliver stimulation and sense intrinsic neuronal signals. System 100 may provide for "closed-loop" therapy where IMD 106 may continuously monitor the state of certain biomarker signals and deliver stimulation according to pre-programmed routines based on the biomarker signals.

System 100 may be configured to treat a patient condition, such as a movement disorder, neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120. In some examples, unipolar stimulation may be possible where one electrode is on the housing of IMD 106.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the neurological signals sensed within brain 120 may reflect changes in electrical current produced by the sum of electrical potential differences across brain tissue. Examples of neurological brain signals include, but are not limited to, bioelectric signals generated from local field potentials (LFP) sensed within one or more regions of brain 120. Electroencephalogram (EEG) signal or an electrocorticogram (ECoG) signal are also examples of bioelectric signals. For example, neurons generate the bioelectric signals, and if measured at depth, it is LFP, if measured on the coretex, it is ECoG, and if on scalp, it is EEG. In this disclosure, the term "oscillatory signal source" may be used to describe one example of a signal source that generates bioelectric signals. However, the bioelectric signals are not limited to oscillatory signals. For example purposes, the techniques are described with oscillatory bioelectric signals from an oscillatory signal source.

One example of the feature of interest (e.g., biomarker) within the LFPs is synchronized beta frequency band (13-33 Hz) LFP activity recorded within the sensorimotor region of the subthalamic nucleus (STN) in Parkinson's disease patients. The source of the LFP activity can be considered as an oscillatory signal source, within the brain of the patient, that outputs an oscillatory electrical voltage signal that is sensed by one or more of electrodes 116 and/or 118. The suppression of pathological beta activity (e.g., suppression or squelching of the signal component of the bioelectric signals generated from the oscillatory LFP signal source that is within the beta frequency band) by both medication and DBS may correlate with improvements in the motor symptoms of patients who have Parkinson's disease. While the beta frequency band is referred to herein, techniques described herein for using LFP activity may apply to other frequency bands (e.g., a theta frequency band).

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both stimulation electrode combinations and sense electrode combinations may be selected from the same set of electrodes 116, 118. In other examples, the electrodes used for delivering electrical stimulation may be different than the electrodes used for sensing neurological brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DB S according to a selected therapy program. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. As described further, the electrical stimulation generated by IMD 106 may generate, for example, burst pulses, interleaved pulses, or concurrent pulses.

In some examples, electrodes 116, 118 may be radially-segmented DBS arrays (rDBSA) of electrodes. Radially-segmented DBS arrays refer to electrodes that are segmented radially along the lead. As one example, leads 114A and 114B may include a first set of electrodes arranged circumferentially around leads 114A and 114B that are all at the same height level on leads 114A and 114B. Each of the electrodes in the first set of electrodes is a separate segmented electrode and form a level of radially-segmented array of electrodes. Leads 114A and 114B may include a second set of electrodes arranged circumferentially around leads 114A and 114B that are all at the same height level on leads 114A and 114B. Each of the electrodes in the first set of electrodes is a separate segmented electrode and form a level of radially-segmented array of electrodes. The rDBSA electrodes may be beneficial for directional stimulation and sensing.

The signal component in the beta frequency band is described as one example, and the techniques are applicable to other types of LFP activity. Furthermore, the example techniques are not limited to examples where electrodes 116, 118 are an rDBSA of electrodes. The example of using rDBSA of electrodes is described as a way of directional stimulation and sensing. However, the example techniques are also useable in examples where directional stimulation and sensing are not available or are not used. Moreover, there may be other ways of performing directional stimulation and sensing that do not require the use of an rDBSA of electrodes.

To suppress the signal component having the beta frequency band from the oscillatory signal source, IMD 106 may output an electrical stimulation signal that alters the way in which neurons of the oscillatory signal source produce signals. For example, the electrical stimulation either directly inhibits a certain neuronal population that includes the oscillatory signal source or excites one group of neurons which in turn suppresses another group of neurons (e.g., network effect). The stimulation may act on the neurons directly, and not necessarily on the signals the neurons (e.g., oscillatory signal source) produces.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres (or in just one hemisphere in some examples), respectively, of patient 112 in order to deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. For example, the target tissue site may be the location of the oscillatory signal source that generates the bioelectric signal having a signal component in the beta frequency band. The stimulation electrodes used to deliver stimulation to the target tissue site may be those that are most proximal to the oscillatory signal source, e.g., using the example techniques described in this disclosure. Other lead 114 and IMD 106 implant sites are contemplated. For example, IMD 106 may be implanted on or within cranium 122, in some examples.

Leads 114A and 114B may be implanted within the same hemisphere or IMD 106 may be coupled to a single lead implanted in a single hemisphere, in some examples.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue.

In some examples, a housing of IMD 106 may include one or more stimulation and/or sensing electrodes. In some examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the parameters of the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

However, in some examples, IMD 106 or programmer 104 (e.g., a medical device), alone or in combination, may automatically determine electrode configuration and therapy parameters. For example, the medical device may determine which electrodes to use for stimulation based on which electrodes are most proximal to the oscillatory signal source. In some examples, programmer 104 may output information indicating the selected electrode configuration for stimulation and the determined stimulation amplitude or other therapy parameter for the clinician or physician to review and confirm before IMD 106 delivers therapy via the selected electrode configuration with the determined stimulation amplitude.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112. Further, an IMD may provide other electrical stimulation such as spinal cord stimulation to treat a movement disorder.

Medication can be provided for treatment of a patient condition, such as a movement disorder, neurodegenerative impairment, a mood disorder, or a seizure disorder of patient 112. Examples of medication that can be provided may include, for example, Levodopa/Carbidopa and its derivatives, Comtan, DA agonists, MAO-B inhibitors, phenobarbital, carbamazepine, oxcarbazepine, possible gabapentin, Baclofen, Tizanidine, Dantrolene sodium, Diazepam, Clonazepam, or other medication. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

In some examples, IMD 106 may be configured to provide electrical stimulation for treatment of a patient condition. For example, IMD 106 may provide treatment supplemental to medication provided to patient 122. Although some examples are described with the use of IMD 106 that provides stimulation, the techniques are not limited and the techniques may apply to examples where no stimulation is provided. For example, IMD 106 may not provide stimulation and treatment of a patient condition of patient 122 may be provided by medication or by medication with other techniques. For instance, IMD 106 may use LFP to determine medication for one disorder of patient 122 and may apply stimulation for another disorder of patient 122. For example, patient 122 may have a dual disease like Parkinson's disease and Dystonia and leads 114 are in locations to treat both Parkinson's disease and Dystonia. A single medical device 106 may listen/monitor to different LFP bands to look at various medication or disease states via the same lead/same hemisphere or different hemispheres.

According to the techniques of the disclosure, a medical device (e.g., IMD 106 or programmer 104 either alone or in combination) of system 100 may be configured to determine, based on LFP activity of patient 122, when patient 122 takes medication. In some examples, the medical device of system 100 may be configured to determine, based on LFP activity of patient 122, a duration of when the medication is effective. The medical device of system 100 may be configured to determine, based on LFP activity of patient 122, both when patient 122 takes medication and a duration of when the medication is effective. The medical device may output an indication of when patient 122 takes the medication and/or the duration of when the medication is effective to facilitate a treatment for the patient. For example, programmer 104 may display the indication of when patient 122 takes the medication and/or the duration of when the medication is effective to facilitate a treatment for the patient on a display of programmer 104.

For example, a medical device (e.g., IMD 106 or programmer 104 either alone or in combination) of system 100 may be configured to determine an indication of when patient 122 takes medication. For instance, the medical device may receive an indication of a user input indicating that patient 122 has taken the medication. In some instances, the medical device may determine that the patient 122 has taken the medication based on the LFP activity of patient 122 (e.g., when an LFP activity decreases by a threshold amount). For example, when a patient takes a drug such as levodopa or a barbiturate, the LFP recordings may be typically reduced in a pattern. With the LFP recordings, the medical device may identify the LFP activity and symptom severity off medication(s) then have patient 122 take their medication(s) to identify how quickly the medication(s) begins to reduce symptoms, how well the efficacy reduces symptoms and how long the medication(s) reduces symptoms. The medical device may monitor other bands such as, for example, a gamma band to determine if the medication (s) are causing dyskinesias (e.g., a side effect of too much medication). In some examples, the medical device may determine when patient 122 takes medication based on both the received indication of the user input indicating that patient 122 has taken the medication and the LFP activity of patient 122.

In this example, a medical device (e.g., IMD 106 or programmer 104 either alone or in combination) of system 100 may determine, based on the LFP activity of patient 122, how quickly the medication is effective for treatment of patient 102. For instance, the medical device may determine that the medication is effective in response to determining that a magnitude of the LFP activity of patient 102 satisfies a threshold (e.g., is less than a threshold). In this example, the medical device may determine, based on LFP activity of patient 122 and after determining that the medication is effective for treatment of patient 102, when the medication is not effective for treatment of patient 102. For instance, the medical device may determine that the medication is not effective in response to determining that a magnitude of the LFP activity of patient 102 does not satisfy the threshold (e.g., is greater than a threshold). The medical device may determine the duration of when the medication is effective based on a time difference between when the medication is effective for treatment of patient 102 and when the medication is no longer effective for treatment of patient 102.

In this way, system 100 may determine an efficacy of medication using an "objective" metric compared to techniques that rely on response from patient 122, which may improve the accuracy of medication information generated by system 100 compared to systems relying only on response from patient 122. That is, determining, based on LFP activity of patient 122, when patient 122 takes medication and/or a duration of when the medication is effective for treatment of patient 122 may generate an indication of medical information for patient 122 that that is not influenced by personal feelings, tastes, or opinions of patient 122 (i.e., a subjective metric). Accordingly, this disclosure describes example ways of having a technical solution to address issues with patient self-reporting, which can be inaccurate. Moreover, the additional medical data relating to the duration of when the medication is effective for treatment of patient 122 based on the LFP activity may be used to determine a progression of a disease of patient 122 (e.g., Parkinson's disease), which allow a selection of electrical stimulation parameters of IMD 106 that improve a treatment provided to patient 122.

Figure 2:
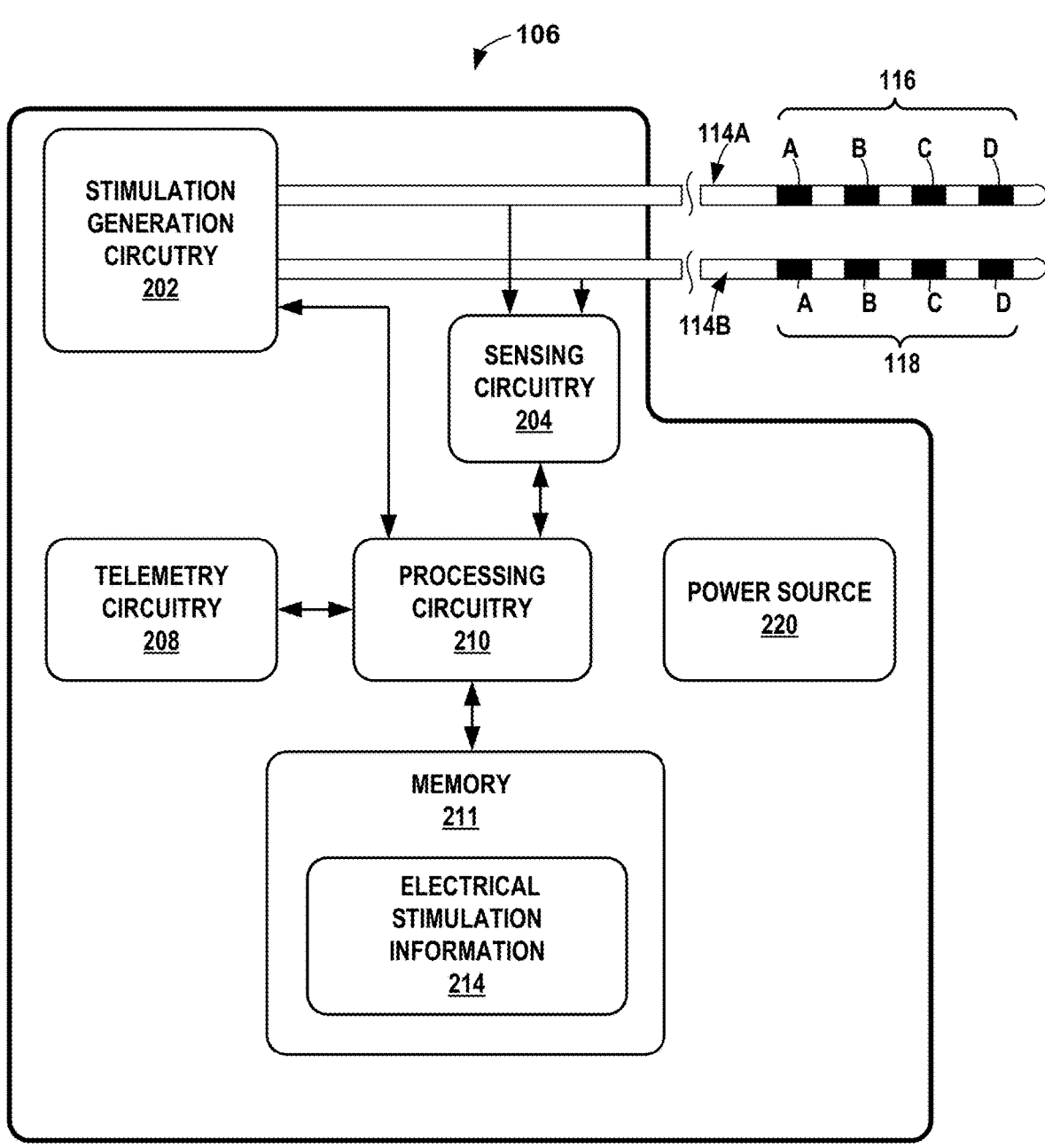
FIG. 2 is a block diagram of the example IMD of FIG. 1 for delivering electrical stimulation according to an example of the techniques of the disclosure.

FIG. 2 is a block diagram of the example IMD 106 of FIG. 1 for delivering adaptive deep brain stimulation therapy. In the example shown in FIG. 2, IMD 106 includes processing circuitry 210, memory 211, stimulation generation circuitry 202, sensing circuitry 204, and telemetry circuitry 208, and power source 220. Each of these circuits may be or include electrical circuitry configured to perform the functions attributed to each respective circuit. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 106 to perform various functions. Memory 211 may be a storage device or other non-transitory medium.

In the example shown in FIG. 2, memory 211 stores electrical stimulation information 214. Electrical stimulation information 214 may include program parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Stimulation generation circuitry 202, under the control of processing circuitry 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 40 Hertz and approximately 500 Hertz, such as between approximately 90 to 170 Hertz or such as approximately 90 Hertz.
2. In the case of a voltage controlled system, Voltage Amplitude: between approximately 0.1 volts and approximately 50 volts, such as between approximately 2 volts and approximately 3 volts.
3. In the case of a current controlled system, Current Amplitude: between approximately 1 milliamps to approximately 3.5 milliamps, such as between approximately 1.0 milliamps and approximately 1.75 milliamps.

4. Pulse Width: between approximately 50 microseconds and approximately 500 microseconds, such as between approximately 50 microseconds and approximately 200 microseconds.

Accordingly, in some examples, stimulation generation circuitry 202 may generate electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processing circuitry 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 may control stimulation generation circuitry 202 according to therapy programs 214 stored in memory 211 to apply particular stimulation parameter values specified by one or more of programs, such as voltage amplitude or current amplitude, pulse width, and/or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 210 may control switch circuitry to apply the stimulation signals generated by stimulation generation circuitry 202 to selected combinations of electrodes 116, 118. In particular, switch circuitry may couple stimulation signals to selected conductors within leads 114, which, in turn, deliver the stimulation signals across selected electrodes 116, 118. The switch circuitry, when used, may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generation circuitry 202 is coupled to electrodes 116, 118 via switch circuitry and conductors within leads 114. In some examples, however, IMD 106 does not include switch circuitry.

Stimulation generation circuitry 202 may be a single channel or multi-channel stimulation generator. In particular, stimulation generation circuitry 202 may be capable of delivering a single stimulation pulse, multiple stimulation pulses, or a continuous signal at a given time via a single electrode combination or multiple stimulation pulses at a given time via multiple electrode combinations. In some examples, however, stimulation generation circuitry 202 may be configured to deliver multiple channels on a time-interleaved basis. For example, switch circuitry may serve to time divide the output of stimulation generation circuitry 202 across different electrode combinations at different times to deliver multiple programs or channels of stimulation energy to patient 112. Alternatively, stimulation generation circuitry 202 may comprise multiple voltage or current sources and sinks that are coupled to respective electrodes to drive the electrodes as cathodes or anodes. In this example, IMD 106 may not require the functionality of switch circuitry for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes, e.g., arranged as segments, at different perimeter locations around the perimeter of the lead at each of the locations A, B, C, and D.

As an example, one or both of leads 114 may include radially-segmented DBS arrays (rDBSA) of electrodes. In the rDBSA, as one example, there may be a first ring electrode of electrodes 116 around the perimeter of lead 114A at a first longitudinal location on lead 114A (e.g., location A). Below the first ring electrode, there may be three segmented electrodes of electrodes 116 around the perimeter of lead 114A at a second longitudinal location on lead 114A (e.g., location B). Below the three segmented electrodes, there may be another set of three segmented electrodes of electrodes 116 around the perimeter of lead 114A at a third longitudinal location of lead 114A (e.g., location C). Below the three segmented electrodes, there may be a second ring electrode of electrodes 116 around the perimeter of lead 114A (e.g., location D). Electrodes 118 may be similarly positioned along lead 114B. An example of rDBSA arrays of electrodes on a lead is described in more detail with respect to FIG. 4.

The above is one example of the rDBSA array of electrodes, and the example techniques should not be considered limited to such an example. There may be other configurations of electrodes for DBS. Moreover, the example techniques are not limited to DBS, and other electrode configurations are possible.

In one example, the electrodes 116, 118 may be electrically coupled to switch circuitry via respective wires that are straight or coiled within the housing of the lead and run to a connector at the proximal end of the lead. In another example, each of the electrodes 116, 118 of the leads 114 may be electrodes deposited on a thin film. The thin film may include an electrically conductive trace for each electrode that runs the length of the thin film to a proximal end connector. The thin film may then be wrapped (e.g., a helical wrap) around an internal member to form the leads 114. These and other constructions may be used to create a lead with a complex electrode geometry.

Although sensing circuitry 204 is incorporated into a common housing with stimulation generation circuitry 202 and processing circuitry 210 in FIG. 2, in other examples, sensing circuitry 204 may be in a separate housing from IMD 106 and may communicate with processing circuitry 210 via wired or wireless communication techniques. Example neurological brain signals include, but are not limited to, a signal generated from local field potentials (LFPs) within one or more regions of brain 120. EEG and ECoG signals are examples of local field potentials that may be measured within brain 120. LFPs, EEG and ECoG may be different measurements of the same bioelectric signals in the brain. The neurons generate the signals, and if measured at depth, it is LFP, if measured on the coretex, it is ECoG, if on the scalp, it is EEG. In general, the bioelectric signals may be formed by one or more oscillatory signal sources. The set of electrodes 116 and 118 that are most proximate to the oscillatory signal sources are good candidates to use for delivering therapy.

Telemetry circuitry 208 supports wireless communication between IMD 106 and an external programmer 104 or another computing device under the control of processing circuitry 210. Processing circuitry 210 of IMD 106 may receive, as updates to programs, values for various stimulation parameters such as magnitude and electrode combination, from programmer 104 via telemetry circuitry 208. The updates to the therapy programs may be stored within therapy programs 214 portion of memory 211. Telemetry circuitry 208 in IMD 106, as well as telemetry modules in other devices and systems described herein, such as programmer 104, may accomplish communication by radiofrequency (RF) communication techniques. In addition, telemetry circuitry 208 may communicate with external medical device programmer 104 via proximal inductive interaction of IMD 106 with programmer 104. Accordingly, telemetry circuitry 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 106. In some examples, power requirements may be small enough to allow IMD 106 to utilize patient motion and implement a kinetic energy-scavenging device to trickle charge a rechargeable battery. In other examples, traditional batteries may be used for a limited period of time.

In one example, processing circuitry 210 of IMD 106 may sense, via electrodes 116, 118 interposed along leads 114 (and sensing circuitry 204), one or more bioelectric signals of brain 120 of patient 112. Further, processing circuitry 210 of IMD 106 may deliver, via electrodes 116, 118 (and stimulation generation circuitry 202), electrical stimulation therapy to patient 112 based on the sensed one or more bioelectric signals of brain 120. The adaptive DBS therapy is defined by electrical stimulation information 214. For example, electrical stimulation information 214 may include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. Processing circuitry 210, via electrodes 116, 118, delivers to patient 112 adaptive DBS and may adjust one or more parameters defining the electrical stimulation based on corresponding parameters of the sensed one or more bioelectric signals of brain 120.

In some examples, processing circuitry 210 may continuously measure the one or more bioelectric signals in real time. In other examples, processing circuitry 210 may periodically sample the one or more bioelectric signals according to a predetermined frequency or after a predetermined amount of time. In some examples, processing circuitry 210 may periodically sample the signal at a frequency of approximately 150 Hertz.

According to the techniques of the disclosure, processing circuitry 210, with sensing circuitry 204, may be configured to generate an indication of LFP activity of patient 122. For instance, processing circuitry 210, with sensing circuitry 204, may be configured to generate an indication of an intensity of LFP activity of patient 122. For instance, processing circuitry 210, with sensing circuitry 204 may sense one or more bioelectric signals of brain 120 of a patient 122 that includes the LFP activity of brain 120 of patient 122. In this instance, stimulation generation circuitry 202 may be configured to generate stimulation signals for delivery to patient 112 via selected combinations of electrodes 116, 118 based on the one or more bioelectric signals sensed using sensing circuitry 204.

IMD 106 and/or programmer 104 may be configured to determine, based on LFP activity of patient 122, one or more of when patient 122 takes medication and a duration of when the medication is effective. IMD 106 and/or programmer 104 may output an indication of when patient 122 takes the medication and/or the duration of when the medication is effective to facilitate a treatment for the patient. For example, IMD 106 may cause programmer 104 to display the indication of when patient 122 takes the medication and/or the duration of when the medication is effective to facilitate a treatment for the patient on a display of programmer 104.

In this way, IMD 106 may help to determine an efficacy of medication using an "objective" metric compared to techniques that rely on response from patient 122, which may improve the accuracy of medication information generated by IMD 106 compared to systems relying only on response from patient 122. That is, determining, based on LFP activity of patient 122, when patient 122 takes medication and/or a duration of when the medication is effective for treatment of patient 122 may generate an indication of medical information for patient 122 that that is not influenced by personal feelings, tastes, or opinions of patient 122 (i.e., a subjective metric). Moreover, the additional medical data relating to the duration of when the medication is effective for treatment of patient 122 based on the LFP activity may be used to determine a progression of a disease of patient 122 (e.g., peritoneal dialysis or Parkinson's), which allow a selection of electrical stimulation parameters of IMD 106 that improve a treatment provided to patient 122.

Figure 3:
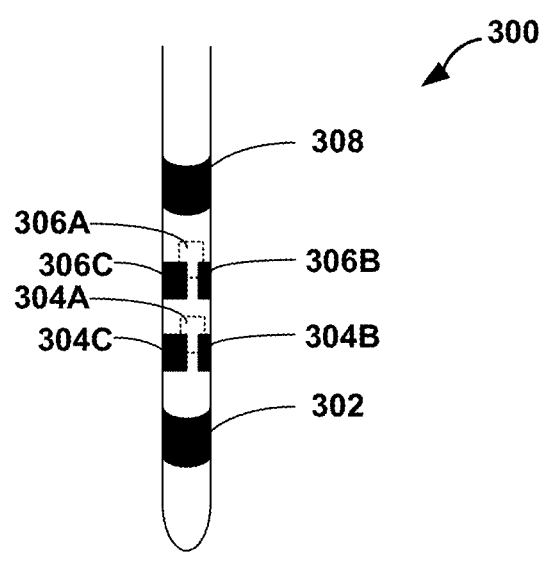
FIG. 3 is a conceptual diagram illustrating an example of a lead with segmented and ring electrodes.

FIG. 3 is a conceptual diagram illustrating an example of a lead 300 with segmented and ring electrodes. Lead 300 is an example of leads 114A and 114B. Processing circuitry 210 may be configured to output electrical signals using, for example, bursts of pulses, interleaved pulses, and/or concurrent pulses at one or more of ring electrode 302, segmented electrodes 304A-304C, segmented electrodes 306A-306C, or ring electrode 308.

The lead radius for lead 300 is approximate 0.66 mm. Lead 300 includes ring electrode 302, segmented electrodes 304A-304C, segmented electrodes 306A-306C, and ring electrode 308. The electrodes on lead 300 may be vertically (e.g., axially) spaced by a distance D (e.g., 2 mm to 3 mm). For example, assume that the z-coordinate for ring electrode 302 is 0. In this example, the z-coordinate for segment electrodes 304A-304C is D, the z-coordinate for segment electrodes 306A-306D is 2D, and the z-coordinate for ring electrode 308 is 3D.

Segmented electrodes 304A-304C may be all at the same vertical level (e.g., axial level), and segmented electrodes 306A-306C may be all at the same vertical level (e.g., axial level). In this example, the angular separation between segmented electrodes 304A-304C may be 120-degrees. Therefore, segmented electrodes 304A and 306A are on the backside of lead 300 and shown in dashed lines.

Figure 4:
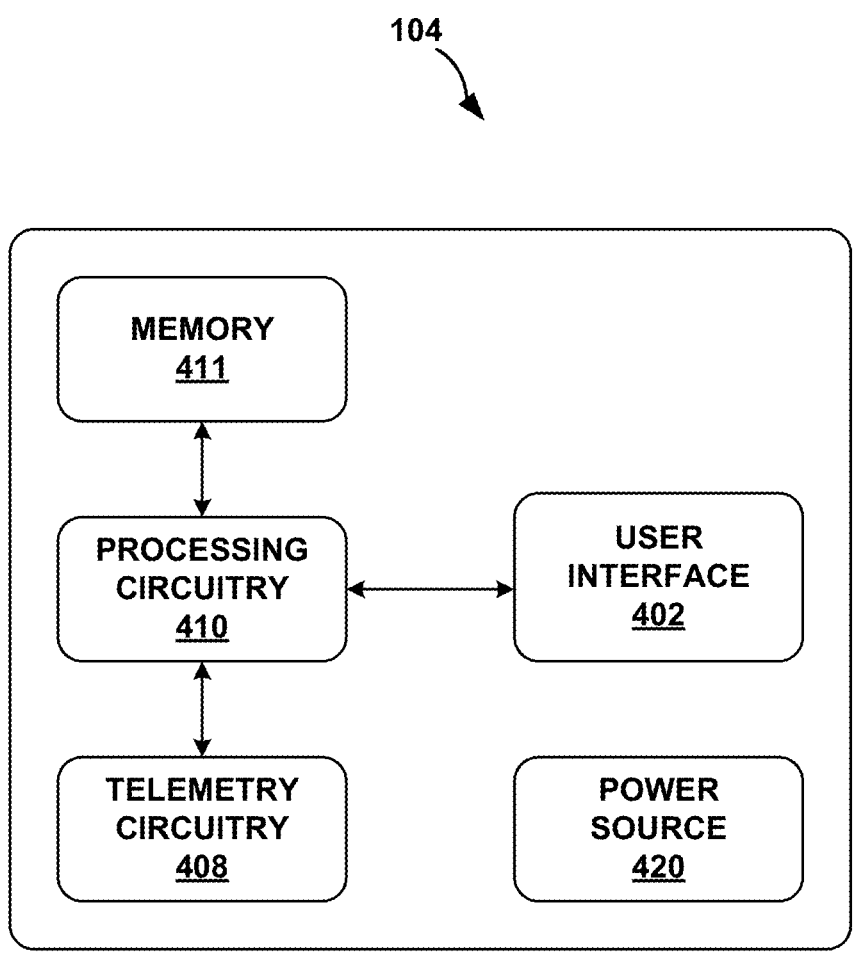
FIG. 4 is a block diagram of the external programmer of FIG. 1 for controlling delivery of electrical stimulation according to an example of the techniques of the disclosure.

FIG. 4 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 4, programmer 104 may include processing circuitry 410, memory 411, user interface 402, telemetry circuitry 408, and power source 420. Memory 411 may store instructions that, when executed by processing circuitry 410, cause processing circuitry 410 and external programmer 104 to provide the functionality ascribed to external programmer 104 throughout this disclosure. Each of these components, or modules, may include electrical circuitry that is configured to perform some or all of the functionality described herein. For example, processing circuitry 410 may include processing circuitry configured to perform the processes discussed with respect to processing circuitry 410.

In general, programmer 104 comprises any suitable arrangement of hardware, alone or in combination with software and/or firmware, to perform the techniques attributed to programmer 104, and processing circuitry 410, user interface 402, and telemetry circuitry 408 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 411, such as RAM, ROM, PROM, EPROM, EEPROM, flash memory, a hard disk, a CD-ROM, comprising executable instructions for causing the one or more processors to perform the actions attributed to them. Moreover, although processing circuitry 410 and telemetry circuitry 408 are described as separate modules, in some examples, processing circuitry 410 and telemetry circuitry 408 may be functionally integrated with one another. In some examples, processing circuitry 410 and telemetry circuitry 408 correspond to individual hardware units, such as ASICs, DSPs, FPGAs, or other hardware units.

Memory 411 (e.g., a storage device) may store instructions that, when executed by processing circuitry 410, cause processing circuitry 410 and programmer 104 to provide the functionality ascribed to programmer 104 throughout this disclosure. For example, memory 411 may include instructions that cause processing circuitry 410 to obtain a parameter set from memory or receive a user input and send a corresponding command to IMD 106, or instructions for any other functionality. In addition, memory 411 may include a plurality of programs, where each program includes a parameter set that defines stimulation therapy.

User interface 402 may include a button or keypad, lights, a speaker for voice commands, a display, such as a liquid crystal (LCD), light-emitting diode (LED), or organic light-emitting diode (OLED). In some examples the display may be a touch screen. User interface 402 may be configured to display any information related to the delivery of stimulation therapy, identified patient behaviors, sensed patient parameter values, patient behavior criteria, or any other such information. User interface 402 may also receive user input. The input may be, for example, in the form of pressing a button on a keypad or selecting an icon from a touch screen.

Telemetry circuitry 408 may support wireless communication between IMD 106 and programmer 104 under the control of processing circuitry 410. Telemetry circuitry 408 may also be configured to communicate with another computing device via wireless communication techniques, or direct communication through a wired connection. In some examples, telemetry circuitry 408 provides wireless communication via an RF or proximal inductive medium. In some examples, telemetry circuitry 408 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection.

In some examples, processing circuitry 410 of external programmer 104 defines the parameters of electrical stimulation therapy, stored in memory 411, for delivering adaptive DB S to patient 112. In one example, processing circuitry 410 of external programmer 104, via telemetry circuitry 408, issues commands to IMD 106 causing IMD 106 to deliver electrical stimulation therapy via electrodes 116, 118 via leads 114.

According to the techniques of the disclosure, programmer 104 may be configured to determine, based on LFP activity of patient 122, when patient 122 takes medication. In some examples, programmer 104 may be configured to determine, based on LFP activity of patient 122, a duration of when the medication is effective. Programmer 104 may be configured to determine, based on LFP activity of patient 122, both when patient 122 takes medication and a duration of when the medication is effective. Programmer 104 may output an indication of when patient 122 takes the medication and/or the duration of when the medication is effective to facilitate a treatment for the patient. For example, programmer 104 may display the indication of when patient 122 takes the medication and/or the duration of when the medication is effective to facilitate a treatment for the patient on a display of programmer 104. In some examples, programmer 104 may output the indication of when patient 122 takes the medication and/or the duration of when the medication is effective to facilitate a treatment to a remote device (e.g., a remote server or remote client).

For example, programmer 104 may be configured to determine an indication of when patient 122 takes medication. For instance, programmer 104 may receive an indication of a user input indicating that patient 122 has taken the medication. In some instances, programmer 104 may determine that the patient 122 has taken the medication based on the LFP activity of patient 122 (e.g., when an LFP activity decreases by a threshold amount) received from IMD 106.

Programmer 104 may determine, based on the LFP activity of patient 122, how quickly the medication is effective for treatment of patient 102. For instance, programmer 104 may determine that the medication is effective in response to determining that a magnitude of the LFP activity of patient 102 satisfies a threshold (e.g., is less than a threshold). In this example, programmer 104 may determine, based on LFP activity of patient 122 and after determining that the medication is effective for treatment of patient 102, when the medication is not effective for treatment of patient 102. For instance, programmer 104 may determine that the medication is not effective in response to determining that a magnitude of the LFP activity of patient 102 does not satisfy the threshold (e.g., is greater than a threshold). Programmer 104 may determine the duration of when the medication is effective based on a time difference between when the medication is effective for treatment of patient 102 and when the medication is no longer effective for treatment of patient 102.

In this way, programmer 104 may determine an efficacy of medication using an "objective" metric compared to techniques that rely on response from patient 122, which may improve the accuracy of medication information generated by system 100 compared to systems relying only on response from patient 122. That is, determining, based on LFP activity of patient 122, when patient 122 takes medication and/or a duration of when the medication is effective for treatment of patient 122 may generate an indication of medical information for patient 122 that that is not influenced by personal feelings, tastes, or opinions of patient 122 (i.e., a subjective metric). Moreover, the additional medical data relating to the duration of when the medication is effective for treatment of patient 122 based on the LFP activity may be used to determine a progression of a disease of patient 122 (e.g., peritoneal dialysis or Parkinson's), which allow a selection of electrical stimulation parameters of IMD 106 that improve a treatment provided to patient 122.

Figure 5:
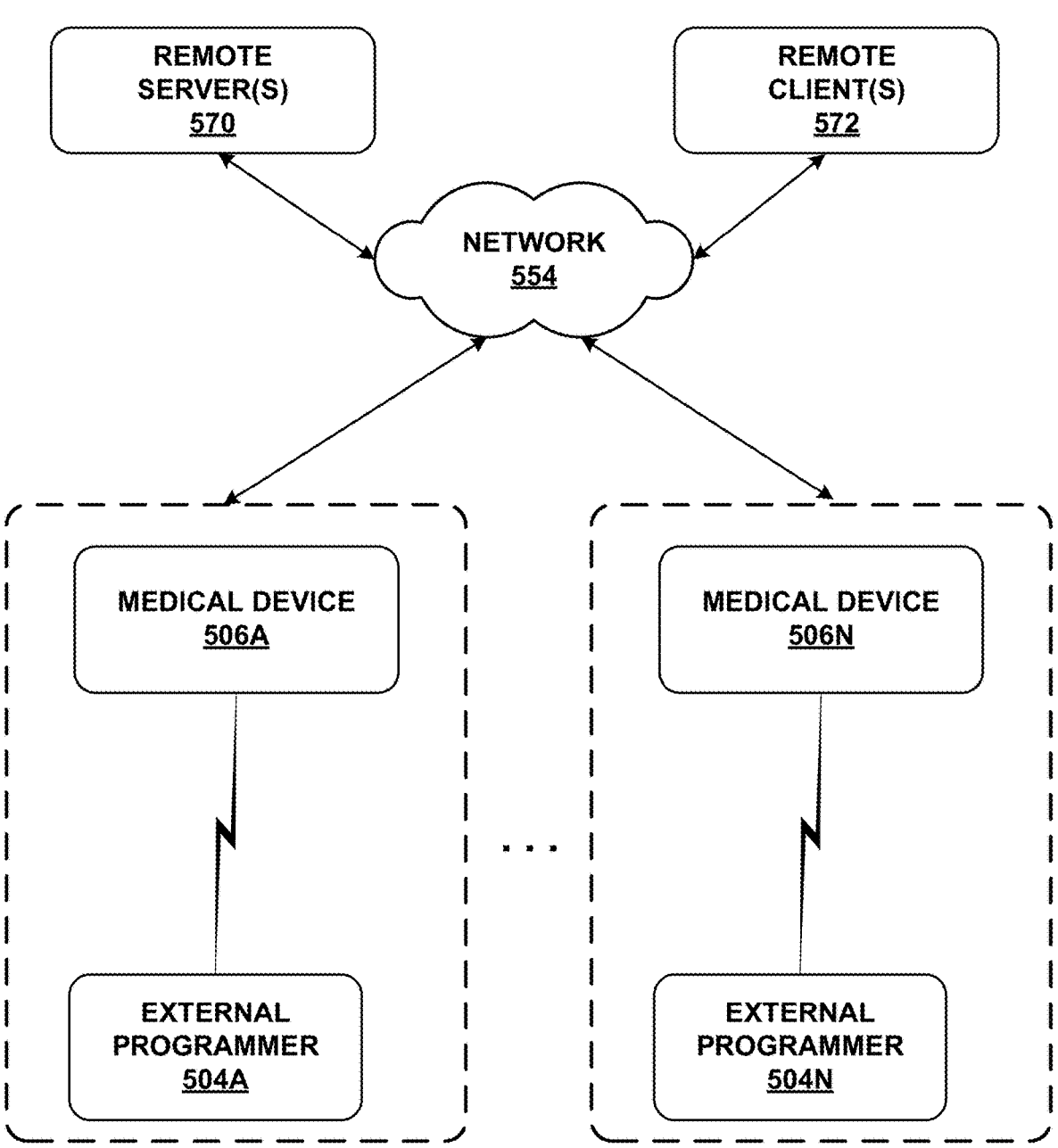
FIG. 5 is a block diagram illustrating an example of one or more remote servers and one or more remote clients suitable for use with the IMD of FIG. 1, in accordance with one or more techniques of this disclosure.

FIG. 5 is a block diagram illustrating an example of one or more remote servers 570 (referred to herein as "remote server 570") and one or more remote clients 572 (referred to herein as "remote clients 572") suitable for use with IMD 106 of FIG. 1, in accordance with one or more techniques of this disclosure. Remote server 570 may represent a cloud computing infrastructure, such as, for example a cloud or web interface. Medical devices 506A-506N (collectively, medical devices 506) and external programmers 504A-504N be associated with patients. For example, medical device 506A and external programmer 504A may be an example of IMD 106 and programmer 104 of FIG. 1 for patient 122 and medical device 506N and external programmer 504N may be associated with another patient different than patient 122.

Remote client 572 may represent a clinician device geographically remote from external programmers 504 and/or medical devices 506. In some examples, remote server 570 may work with remote client 572. For instance, remote server 570 may store data or at least partially process data for remote client 572. Remote client 572 may be used by a health professional at a doctor's office and the patient and medical devices 506 may be at a home of the patient. Remote server 570 and/or remote client 572 may be referred to herein as a remote device. Network 554 may comprise one or more wired (e.g., Ethernet) and/or wireless networks (e.g., Wi-Fi™ Bluetooth™, Zigbee™, IEEE 802.11, etc.). In some examples, network 554 may comprise the Internet. While the previous examples refer to remote client 572 as performing various processes, any combination of medical devices, external programmers 550, remote server 570, or remote client 572 may perform such processes. Moreover, remote client 572 (or any combination of medical devices, external programmers 550, remote server 570, or remote client 572) may perform the processes described as being performed by external programmer 104.

A remote device (e.g., remote server 570 and/or remote client 572) may be configured to control IMD 106 to provide stimulation. For example, the remote device may automatically or semi-automatically set or adjust programs at medical devices 506. For instance, the remote device may receive sensor information or user input information from medical device 506A or external programmers 504A via the network 454 that indicates a change in activity of the patient. While the following examples refer to remote client 572 as performing processes directed to determining when a patient takes medication and/or a duration that the medication is effective for treating the patient, any combination of medical devices 510, external programmers 450, remote server 470, or remote client 472 may perform processes described herein directed to identifying problem patients, initiating a diagnostic test, prioritizing a delivery of data, scheduling a virtual appointments.

In accordance with the techniques of the disclosure, remote client 572 may be configured to determine, based on LFP activity of patient 122, when patient 122 takes medication. In some examples, remote client 572 may be configured to determine, based on LFP activity of patient 122, a duration of when the medication is effective. Remote client 572 may be configured to determine, based on LFP activity of patient 122, both when patient 122 takes medication and a duration of when the medication is effective. Remote client 572 may output an indication of when patient 122 takes the medication and/or the duration of when the medication is effective to facilitate a treatment for the patient. For example, remote client 572 may display the indication of when patient 122 takes the medication and/or the duration of when the medication is effective to facilitate a treatment for the patient on a display.

For example, remote client 572 may be configured to determine an indication of when patient 122 takes medication. For instance, remote client 572 may receive an indication of a user input indicating that patient 122 has taken the medication. In some instances, remote client 572 may determine that a patient 122 has taken the medication based on the LFP activity of the patient (e.g., when an LFP activity decreases by a threshold amount) received from medical devices 506.

Remote client 572 may determine, based on the LFP activity of the patient, how quickly the medication is effective for treatment of the patient. For instance, remote client 572 may determine that the medication is effective in response to determining that a magnitude of the LFP activity of the patient satisfies a threshold (e.g., is less than a threshold). In this example, remote client 572 may determine, based on LFP activity of the patient and after determining that the medication is effective for treatment of the patient, when the medication is not effective for treatment of patient 102. For instance, remote client 572 may determine that the medication is not effective in response to determining that a magnitude of the LFP activity of the patient does not satisfy the threshold (e.g., is greater than a threshold). Remote client 572 may determine the duration of when the medication is effective based on a time difference between when the medication is effective for treatment of the patient and when the medication is no longer effective for treatment of the patient.

In this way, remote client 572 may determine an efficacy of medication using an "objective" metric compared to techniques that rely on response from the patient, which may improve the accuracy of medication information generated by remote client 572 compared to systems relying only on response from the patient. That is, determining, based on LFP activity of the patient, when the patient takes medication and/or a duration of when the medication is effective for treatment of the patient may generate an indication of medical information for the patient that that is not influenced by personal feelings, tastes, or opinions of the patient (i.e., a subjective metric). Moreover, the additional medical data relating to the duration of when the medication is effective for treatment of the patient based on the LFP activity may be used to determine a progression of a disease of the patient (e.g., Parkinson's), which allow a selection of electrical stimulation parameters of medical devices 506 that improve a treatment provided to patients.

Although shown as separate entities, in some examples, functionality may be distributed differently than that shown in FIG. 5. For example, remote server 570 and remote client 572 may be the same system. While the previous examples refer to remote client 572 as performing various processes, any combination of medical devices, external programmers 550, remote server 570, or remote client 572 may perform such processes.

Figure 6:
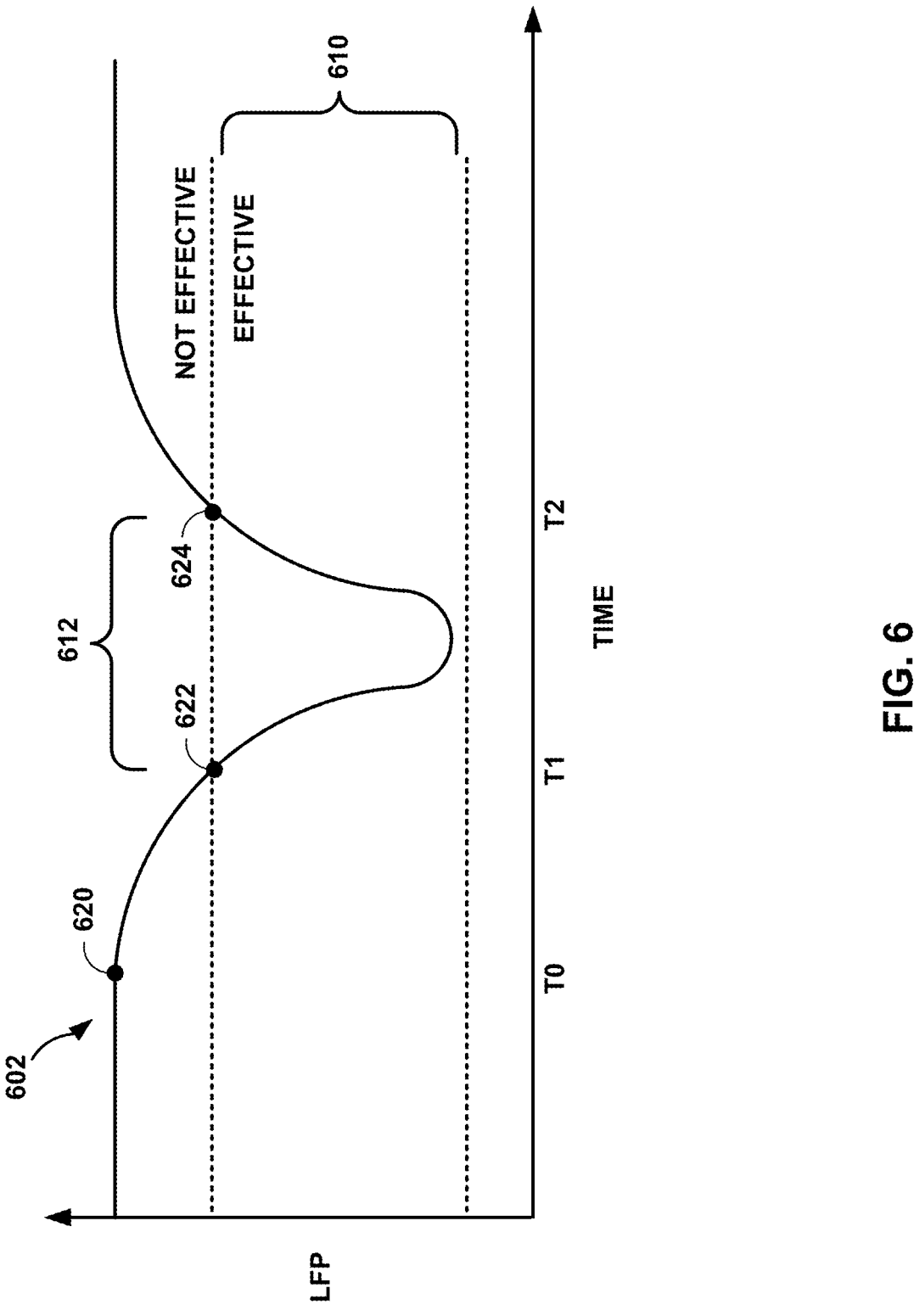
FIG. 6 is a plot illustrating an example of determining a duration of when medication is effective based on LFP activity of a patient according to an example of the techniques of the disclosure.

FIG. 6 is a plot illustrating an example of determining a duration of when medication is effective based on LFP activity 602 of a patient according to an example of the techniques of the disclosure. The ordinate axis of FIG. 6 represents an LFP activity level 602 of patient 122 and the abscissa axis of FIG. 6 represents time. In the example of FIG. 6, patient 122 may take the medication at a first time 620 ("T0"). Programmer 104 may be configured to determine, based on LFP activity 602, when patient 122 takes medication. In some examples, programmer 104 may receive an indication of a user input indicating that patient 122 has taken the medication.

Programmer 104 may be configured to determine, based on LFP activity 602 of patient 122, a duration 612 of when the medication is effective. For example, programmer 104 may determine, based on LFP activity 602 of patient 122, how quickly the medication is effective for treatment of patient 102. For instance, programmer 104 may determine that the medication is effective at a second time 622 ("T1") in response to determining that a magnitude of the LFP activity 602 of patient 102 satisfies a range of LFP values 610 (e.g., is within the range of LFP values 610). In this example, programmer 104 may determine, based on LFP activity 602 of patient 122 and after determining that the medication is effective for treatment of patient 102 (i.e., second time 622), when the medication is not effective for treatment of patient 102. For instance, programmer 104 may determine that the medication is not effective at a third time 624 ("T2") in response to determining that a magnitude of LFP activity 602 of patient 102 does not satisfy range of LFP values 610 (e.g., is outside of range of LFP values 610 or greater than range of LFP values 610). Programmer 104 may determine duration 612 of when the medication is effective based on a time difference between when the medication is effective for treatment of patient 102 (e.g., second time 622) and when the medication is no longer effective for treatment of patient 102 (e.g., third time 624).

Programmer 104 may output an indication of when patient 122 takes the medication (e.g., first time 620) and/or duration 612. For example, programmer 104 may display one or more indications of first time 620 and/or duration 612 on a display of programmer 104. In some examples, programmer 104 may output the one or more indications of first time 620 and/or duration 612 to a remote device (e.g., a remote server or remote client).

Figure 7:
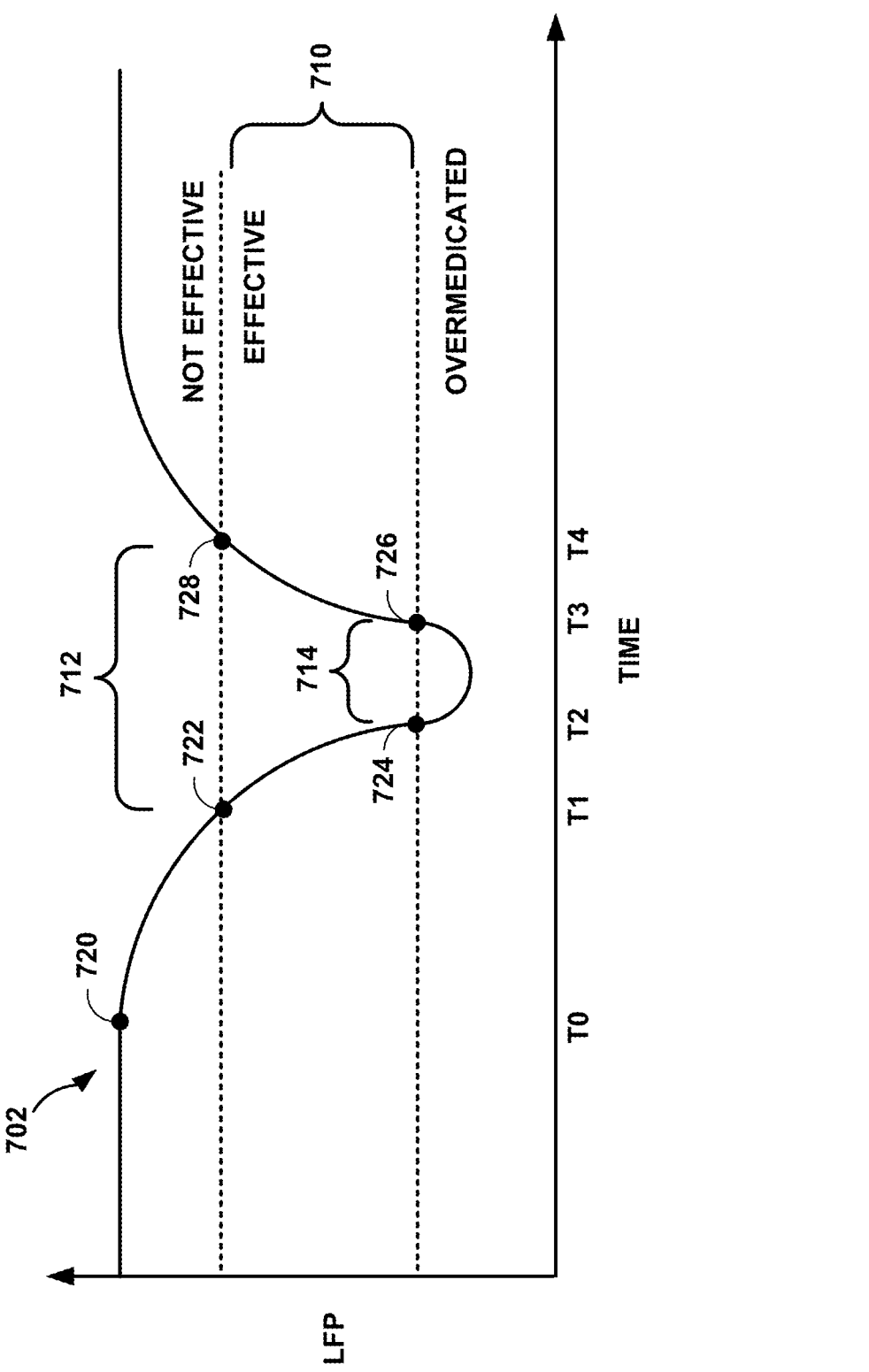
FIG. 7 is a plot illustrating an example of determining that a patient is overmedicated according to an example of the techniques of the disclosure.

FIG. 7 is a plot illustrating an example of determining that a patient is overmedicated according to an example of the techniques of the disclosure. The ordinate axis of FIG. 7 represents an LFP activity level 702 of patient 122 and the abscissa axis of FIG. 7 represents time. In the example of FIG. 7, patient 122 may take the medication at a first time 720 ("T0"). Programmer 104 may be configured to determine, based on LFP activity 702, when patient 122 takes medication. In some examples, programmer 104 may receive an indication of a user input indicating that patient 122 has taken the medication.

Programmer 104 may be configured to determine, based on LFP activity 702 of patient 122, a duration 712 of when the medication is effective. For example, programmer 104 may determine, based on LFP activity 702 of patient 122, how quickly the medication is effective for treatment of patient 102. For instance, programmer 104 may determine that the medication is effective at a second time 722 ("T1") in response to determining that a magnitude of the LFP activity 702 of patient 102 satisfies a range of LFP values 710 (e.g., is within range of LFP values 710 or is greater than range of LFP values 710).

Programmer 104 may determine, based on LFP activity 702 of patient 122 and after the patient takes the medication (e.g., first time 720), that patient 122 is overmedicated by the medication. For instance, programmer 104 may determine that patient 122 is overmedicated at a third time 724 ("T2") in response to determining that a magnitude of LFP activity 702 of patient 102 is less than range of LFP values 710. Programmer 104 may determine, based on LFP activity 702 of patient 122 and after the determination that patient 122 is overmedicated (e.g., third time 724), that patient 122 is no longer overmedicated by the medication. For instance, programmer 104 may determine that patient 122 is no longer overmedicated at a fourth time 726 ("T3") in response to determining that a magnitude of LFP activity 702 of patient 102 is within range of LFP values 710.

Programmer 104 may determine, based on LFP activity 702 of patient 122 and after determining that the medication is effective for treatment of patient 102 (i.e., second time 722), when the medication is not effective for treatment of patient 102 and when patient 122 is not overmedicated. For instance, programmer 104 may determine that the medication is not effective and patient 122 is not overmedicated at a fifth time 728 ("T4") in response to determining that a magnitude of LFP activity 602 of patient 102 does not satisfy range of LFP values 610 (e.g., is greater than range of LFP values 610). Programmer 104 may determine duration 712 of when the medication is effective and when patient 122 is overmedicated based on a time difference between when the medication is effective for treatment of patient 102 (e.g., second time 722) and when the medication is no longer effective for treatment of patient 102 (e.g., fifth time 728). In some examples, programmer 104 may determine a duration for when medication is effective and when patient 122 is not overmedicated based on a difference between the duration 712 and duration 714. For instance, programmer 104 may subtract duration 714 from duration 712 to determine when medication is effective and when patient 122 is not overmedicated.

Programmer 104 may output an indication of one or more of when patient 122 takes the medication (e.g., first time 720), duration 712, duration 714, or a difference between the duration 712 and duration 714. For example, programmer 104 may display one or more indications of one or more of first time 720, duration 712, duration 714, or a difference between the duration 712 and duration 714 on a display of programmer 104. In some examples, programmer 104 may output the one or more indications of one or more of first time 720, duration 712, duration 714, or a difference between the duration 712 and duration 714 to a remote device (e.g., a remote server or remote client).

Figure 8:
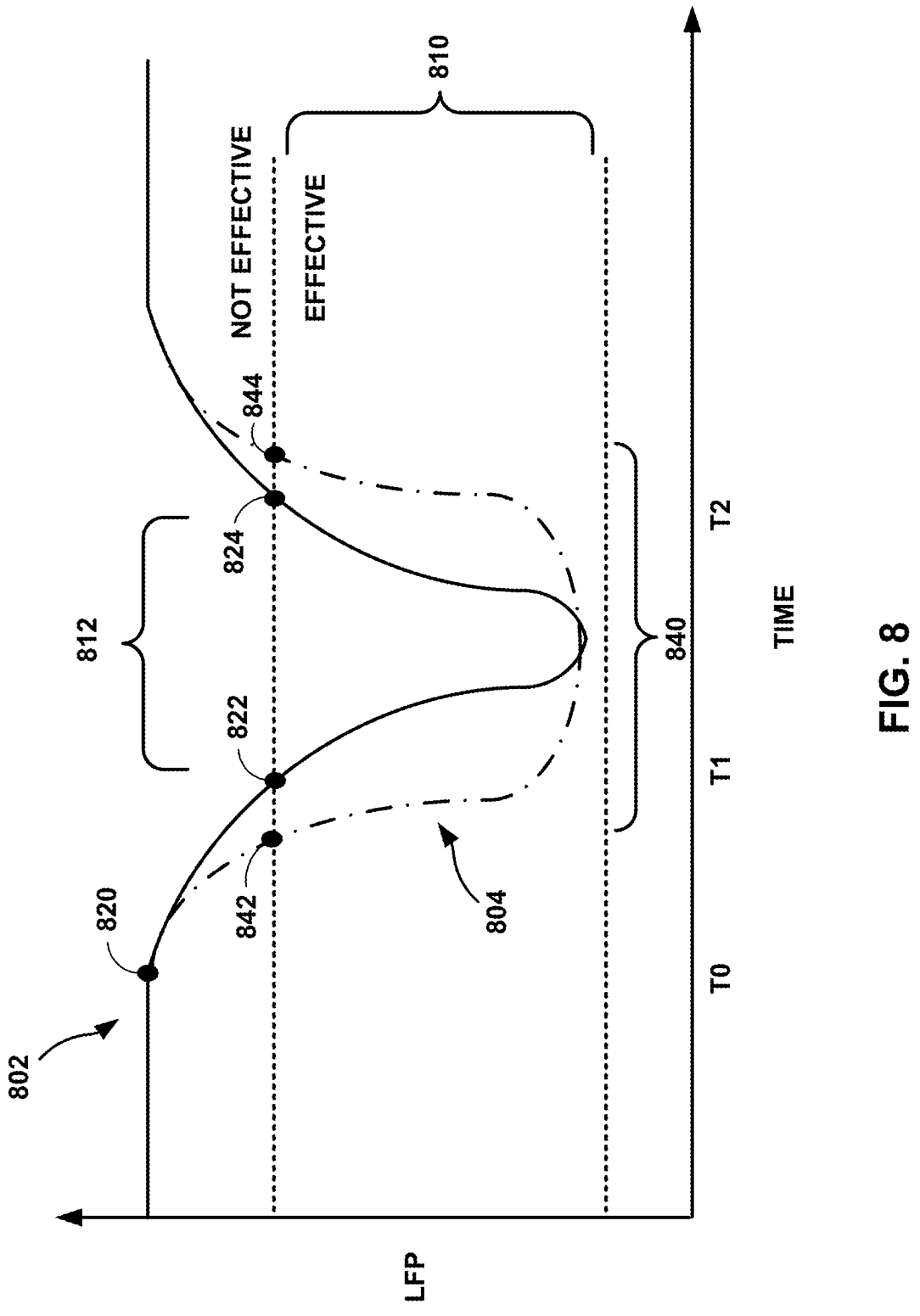
FIG. 8 is a plot illustrating an example of determining whether a first medication or second medication results in a longer effective duration and/or more effective symptom control according to an example of the techniques of the disclosure.

FIG. 8 is a plot illustrating an example of determining whether a first medication or second medication results in a longer effective duration and/or more effective symptom control according to an example of the techniques of the disclosure. The ordinate axis of FIG. 8 represents a first LFP activity level 802 of patient 122 for a first medication and a second LFP activity level 804 of patient 122 for a second medication and the abscissa axis of FIG. 8 represents time. In the example of FIG. 8, patient 122 may take the first medication at an initial time 820 ("T0"). In the example of FIG. 8 during a different time period (e.g., a different day), patient 122 may take the second medication at an initial time 820 ("T0"), which is overlayed with first LFP activity level 802 in FIG. 8 for illustrative purposes.

Using first LFP activity level 802 and second LFP activity level 804, system 100 may determine how well one or more of the stimulation, the medication, or both the stimulation and the medication is working as LFP reduction may equate to symptom reduction. First LFP activity level 802 and second LFP activity level 804 may allow the healthcare provider to see the effectiveness of medications that may extend the efficacy of certain drugs or new drugs that may have a longer duration of action. For example, system 100 could utilize a timeline view to display the various medications overlayed on each other to allow the user to see the impact of the medication changes. The healthcare provider may denote the new medication/time/date that the medication was implemented. In this way, system 100 can determine when the medications were changed/implemented and overlay LFP timeline segments (e.g., first LFP activity level 802 and second LFP activity level 804).

System 100 may determine, based on first LFP activity 802 of patient 122, whether the first medication is more effective than another medication (e.g., a second medication). For example, programmer 104 may be configured to determine, based on first LFP activity 802 of patient 122, a duration 812 of when the first medication is effective. For example, programmer 104 may determine, based on first LFP activity 802 of patient 122, how quickly the first medication is effective for treatment of patient 102. For instance, programmer 104 may determine that the medication is effective at a second time 822 ("T1") in response to determining that a magnitude of the LFP activity 802 of patient 102 satisfies a range of LFP values 810 (e.g., is within the range of LFP values 810). In this example, programmer 104 may determine, based on first LFP activity 802 of patient 122 and after determining that the first medication is effective for treatment of patient 102 (i.e., second time 822), when the first medication is not effective for treatment of patient 102. For instance, programmer 104 may determine that the first medication is not effective at a third time 824 ("T2") in response to determining that a magnitude of first LFP activity 802 of patient 102 does not satisfy range of LFP values 810 (e.g., is outside of range of LFP values 810 or greater than range of LFP values 810). Programmer 104 may determine duration 812 of when the first medication is effective based on a time difference between when the first medication is effective for treatment of patient 102 (e.g., second time 822) and when the first medication is no longer effective for treatment of patient 102 (e.g., third time 824).

Similarly, programmer 104 may be configured to determine, based on second LFP activity 804 of patient 122, a duration 842 of when the second medication is effective. For example, programmer 104 may determine, based on second LFP activity 804 of patient 122, how quickly the second medication is effective for treatment of patient 102. For instance, programmer 104 may determine that the second medication is effective at a second time 842 in response to determining that a magnitude of the second LFP activity 804 of patient 102 satisfies a range of LFP values 810 (e.g., is within the range of LFP values 810). In this example, programmer 104 may determine, based on second LFP activity 804 of patient 122 and after determining that the second medication is effective for treatment of patient 102 (i.e., second time 842), when the second medication is not effective for treatment of patient 102. For instance, programmer 104 may determine that the second medication is not effective at a third time 844 in response to determining that a magnitude of second LFP activity 804 of patient 102 does not satisfy range of LFP values 810 (e.g., is outside of range of LFP values 810 or greater than range of LFP values 810). Programmer 104 may determine duration 840 of when the second medication is effective based on a time difference between when the second medication is effective for treatment of patient 102 (e.g., second time 842) and when the first medication is no longer effective for treatment of patient 102 (e.g., third time 844).

Programmer 104 may output an indication of whether the first medication or the second medication is more effective. For example, programmer 104 may output an indication of one or more of first time 820, second time 822, third time 824, duration 812 for the first medication and one or more of first time 820, second time 842, third time 844, duration 840 for the second medication. For instance, programmer 104 may output an indication of the plot or a portion (e.g., LFP timeline segments) of the plot shown in FIG. 8. In some examples, programmer 104 may output an indication of one or more of first time 820, second time 822, third time 824, duration 812 for the first medication and one or more of first time 820, second time 842, third time 844, duration 840 for the second medication to a remote device (e.g., a remote server or remote client).

System 100 may provide a percent change in LFP activity within the chosen threshold (e.g., dual) vs outside the threshold, or a time above/below the single threshold along with potential stimulation reduction so the user knows if the medication was better, worse or the same compared to the earlier drug/stim combo. For example, system 100 may determine a percent change in LFP activity within range of LFP values 810 compared to outside range of LFP values 810 of first LFP activity 802 for the first medication and second LFP activity 804 for the second medication. For instance, system 100 may calculate the percent change in LFP activity as a difference between duration 812 and duration 840 divided by a time window (e.g., T0 to T2). Programmer 104 may output an indication of the percent change in LFP activity.

In some examples, system 100 may determine a time above and/or below a LFP threshold value (e.g., a value of range of LFP values 810) and/or an indication of a stimulation reduction when using the second medication. For example, system 100 may determine a first duration that first LFP 802 is above a threshold value (e.g., the highest value of range of LFP values 810) and determine a second duration that second LFP 804 is above the threshold value. In some examples, system 100 may determine a first duration that first LFP 802 is below a threshold value (e.g., the highest value of range of LFP values 810) and determine a second duration that second LFP 804 is below the threshold value. System 100 may determine indication of a stimulation reduction based on a difference between a first value for stimulation parameter (e.g., an amplitude) when using the first medication and a second value for the stimulation parameter when using the second medication.

Determining one or more of the indication of whether the first medication or the second medication is more effective, the percent change, the time above and/or below a LFP threshold value, or the indication of a stimulation reduction may help the healthcare provider to effectively titrate (e.g., change) various medication combinations in relation to stimulation settings, LFP, and/or symptom reduction effectiveness. LFP sensing can provide the healthcare provider with how effective a given medication or combination of medications are suppressing LFP, how quickly the medication or combination of medications suppress the LFP, and/or how long the medication or combination of medications suppress the LFP. System 100 could also store the best medication or combination of medication that reduced LFP and compare new meds/combo to that as a baseline to identify if the new combo is better, worse or the same (see FIG. 11).

While a duration that a medication is effective is discussed above. System 100 may provide a healthcare provider all data not just if is if the duration is better. For example, the medication may be almost as good as another medication but without side effects, whereas patient 122 may have been taking the current medication and getting side effects. In this example, system 100 may be configured to show, if enabled, how a new medication is compared (e.g., better, worse or the same) to an old medication in all aspects. For instance, system 100 may receive patient reported outcomes for patient 102 and output the patient reported outcomes with the duration information and optionally with other data for patient 122.

System 100 could remind patient 102 when patient 102 should take the medications. For example, system 100 may cause a device (e.g., programmer 104 (e.g., a patient programmer), IMD 106 (e.g., an INS) to beep or vibrate. While the above example referred to duration 812 as an indication of an effectiveness of treatment, other characteristics of first LFP activity level 802 may be used. For example, a minimum or maximum value of first LFP activity level 802 may indicate an effectiveness of treatment. In some examples, system 100 may determine an effectiveness of treatment based on a patient reported outcome. For instance, system 100 may determine an effectiveness of treatment based on first LFP activity level 802 and further based on the patient reported outcome (e.g., an indication of how the patient is feeling).

Figure 9:
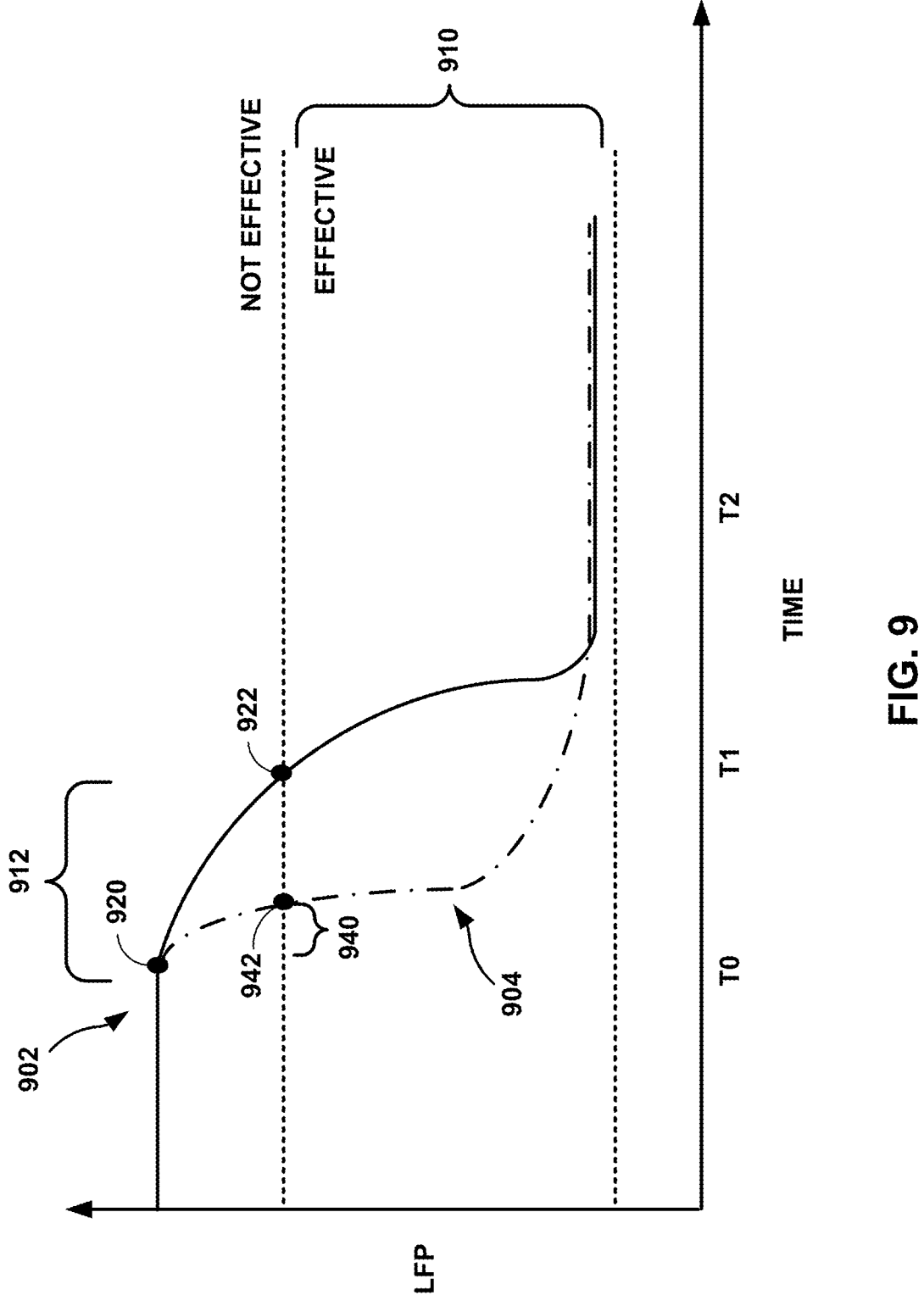
FIG. 9 is a plot illustrating an example of determining whether a first stimulation or second stimulation results in a longer effective duration and/or more effective symptom control according to an example of the techniques of the disclosure.

FIG. 9 is a plot illustrating an example of determining whether a first stimulation or second stimulation results in a longer effective duration and/or more effective symptom control according to an example of the techniques of the disclosure. The ordinate axis of FIG. 9 represents a first LFP activity level 902 of patient 122 for a first stimulation and a second LFP activity level 904 of patient 122 for a second stimulation and the abscissa axis of FIG. 9 represents time. In the example of FIG. 9, system 100 may apply the first stimulation to patient 122 at an initial time 920 ("T0"). In the example of FIG. 9 during a different time period (e.g., a different day), system 100 may apply the second stimulation to patient 122 at initial time 920, which is overlayed with first LFP activity level 902 in FIG. 9 for illustrative purposes.

Using first LFP activity level 902 and second LFP activity level 904, system 100 may determine how well the first stimulation and the second stimulation is working as LFP reduction may equate to symptom reduction. First LFP activity level 902 and second LFP activity level 904 may allow the healthcare provider to see the effectiveness of stimulation. For example, system 100 could utilize a timeline view to display the various stimulations overlayed on each other to allow the user to see the impact of stimulation changes. System 100 can overlay LFP timeline segments (e.g., first LFP activity level 902 and second LFP activity level 904).

For example, programmer 104 may be configured to determine, based on first LFP activity 902 of patient 122, a duration 912 of when the first stimulation is effective. For example, programmer 104 may determine, based on first LFP activity 902 of patient 122, how quickly the first stimulation is effective for treatment of patient 102. For instance, programmer 104 may determine that the first stimulation is effective at a second time 922 ("T1") in response to determining that a magnitude of first LFP activity 902 of patient 102 satisfies a range of LFP values 910 (e.g., is within the range of LFP values 910). In this example, programmer 104 may determine, based on first LFP activity 902 of patient 122 and after determining that the first stimulation is effective for treatment of patient 102 (e.g., at second time 922) that the first stimulation is effective after first duration 912. Programmer 104 may determine first duration 912 of when the first stimulation is effective based on a time difference between when the first stimulation is applied (e.g., first time 920) and when the first stimulation is effective for treatment of patient 102 (e.g., second time 922).

Similarly, programmer 104 may be configured to determine, based on second LFP activity 904 of patient 122, a duration 940 of when the second stimulation is effective. For example, programmer 104 may determine, based on second LFP activity 904 of patient 122, how quickly the second stimulation is effective for treatment of patient 102. For instance, programmer 104 may determine that the second stimulation is effective at a second time 942 in response to determining that a magnitude of second LFP activity 904 of patient 102 satisfies a range of LFP values 910 (e.g., is within the range of LFP values 910). In this example, programmer 104 may determine, based on second LFP activity 904 of patient 122 and after determining that the second stimulation is effective for treatment of patient 102 (e.g., at second time 942) that the second stimulation is effective after second duration 940. Programmer 104 may determine second duration 940 of when the second stimulation is effective based on a time difference between when the second stimulation is applied (e.g., first time 920) and when the second stimulation is effective for treatment of patient 102 (e.g., second time 942).

Programmer 104 may output an indication of whether the first stimulation or the second stimulation is more effective. For example, programmer 104 may output an indication of one or more of first time 920, second time 922, first duration 912 for the first stimulation and one or more of first time 920, second time 942, or second duration 940 for the second stimulation. For instance, programmer 104 may output an indication of the plot or a portion (e.g., LFP timeline segments) of the plot shown in FIG. 9. In some examples, programmer 104 may output an indication of one or more of first time 920, second time 922, first duration 912 for the first stimulation and one or more of first time 920, second time 942, or second duration 940 for the second stimulation to a remote device (e.g., a remote server or remote client).

Figure 10:
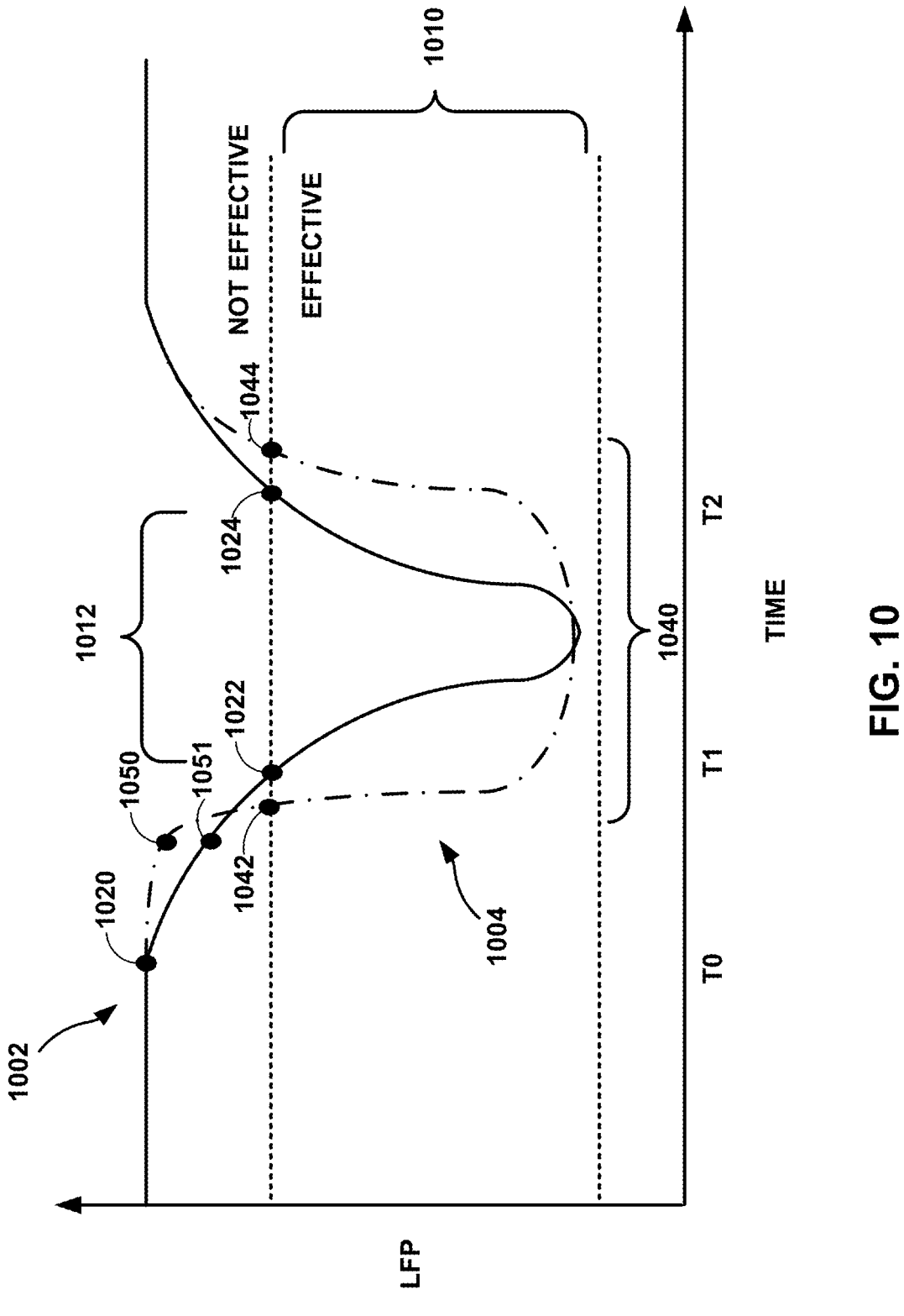
FIG. 10 is a plot illustrating an example of determining whether a first stimulation and medication combination or second first stimulation and medication combination results in a longer effective duration and/or more effective symptom control according to an example of the techniques of the disclosure.

FIG. 10 is a plot illustrating an example of determining whether a first stimulation and medication combination or second first stimulation and medication combination results in a longer effective duration and/or more effective symptom control according to an example of the techniques of the disclosure. The ordinate axis of FIG. 10 represents a first LFP activity level 1002 of patient 122 for a first stimulation and medication combination and a second LFP activity level 1004 of patient 122 for a second stimulation and medication combination and the abscissa axis of FIG. 10 represents time. In the example of FIG. 10, patient 122 may take the first medication at an initial time 1020 ("T0"). In the example of FIG. 10 during a different time period (e.g., a different day), patient 122 may take the second medication at an initial time 1020, which is overlayed with first LFP activity level 802 in FIG. 10 for illustrative purposes. In the example of FIG. 10, the first medication and the second medication are different. However, in some examples, the first medication and the second medication are the same.

In the example of FIG. 10, system 100 may apply the first stimulation to patient 122 at a time 1050. In the example of FIG. 10 during the different time period, system 100 may apply the second stimulation to patient 122 at time 1051, which may correspond to time 1050. In the example of FIG. 10, the first stimulation and the second stimulation are the same. For example, the first stimulation and the second stimulation may both have a same amplitude. However, in some examples, the first stimulation and the second stimulation may be different (e.g., may have different amplitudes).

Using first LFP activity level 1002 and second LFP activity level 1004, system 100 may determine how well the first stimulation and medication combination and the second stimulation and medication combination is working as LFP reduction may equate to symptom reduction. First LFP activity level 1002 and second LFP activity level 1004 may allow the healthcare provider to see the effectiveness of stimulation. For example, system 100 could utilize a time-line view to display the various stimulations overlayed on each other to allow the user to see the impact of stimulation changes. System 100 can overlay LFP timeline segments (e.g., first LFP activity level 1002 and second LFP activity level 1004).

System 100 may determine, based on first LFP activity 802 of patient 122, whether a combination of medication and stimulation is more effective than another combination of medication and stimulation. For example, programmer 104 may be configured to determine, based on first LFP activity 1002 of patient 122, a duration 1012 of when the first stimulation and medication combination is effective. For example, programmer 104 may determine, based on first LFP activity 1002 of patient 122, how quickly the first stimulation and medication combination is effective for treatment of patient 102. For instance, programmer 104 may determine that the first stimulation and medication combi-nation is effective at a second time 1022 ("T1") in response to determining that a magnitude of the first LFP activity 1002 of patient 102 satisfies a range of LFP values 1010 (e.g., is within the range of LFP values 1010). In this example, programmer 104 may determine, based on first LFP activity 1002 of patient 122 and after determining that the first stimulation and medication combination is effective for treatment of patient 102 (e.g., second time 1022), when the first stimulation and medication combination is not effective for treatment of patient 102. For instance, program-mer 104 may determine that the first stimulation and medi-cation combination is not effective at a third time 1024 ("T2") in response to determining that a magnitude of first LFP activity 1002 of patient 102 does not satisfy range of LFP values 1010 (e.g., is outside of range of LFP values 1010 or greater than range of LFP values 1010). Programmer 104 may determine duration 1012 of when the first stimu-lation and medication combination is effective based on a time difference between when the first stimulation and medication combination is effective for treatment of patient 102 (e.g., second time 1022) and when the first stimulation and medication combination is no longer effective for treat-ment of patient 102 (e.g., third time 1024).

Similarly, programmer 104 may be configured to deter-mine, based on second LFP activity 1004 of patient 122, a duration 1040 of when the second stimulation and medica-tion combination is effective. For example, programmer 104 may determine, based on second LFP activity 1004 of patient 122, how quickly the second stimulation and medi-cation combination is effective for treatment of patient 102. For instance, programmer 104 may determine that the sec-ond stimulation and medication combination is effective at a second time 1042 in response to determining that a magnitude of the second LFP activity 1004 of patient 102 satisfies a range of LFP values 1010 (e.g., is within the range of LFP values 1010). In this example, programmer 104 may determine, based on second LFP activity 1004 of patient 122 and after determining that the second stimulation and medi-cation combination is effective for treatment of patient 102 (e.g., second time 1042), when the second stimulation and medication combination is not effective for treatment of patient 102. For instance, programmer 104 may determine that the second stimulation and medication combination is not effective at a third time 1044 in response to determining that a magnitude of second LFP activity 1004 of patient 102 does not satisfy range of LFP values 1010 (e.g., is outside of range of LFP values 1010 or greater than range of LFP values 1010). Programmer 104 may determine duration 1040 of when the second stimulation and medication com-bination is effective based on a time difference between when the second stimulation and medication combination is effective for treatment of patient 102 (e.g., second time 1042) and when the first stimulation and medication com-bination is no longer effective for treatment of patient 102 (e.g., third time 1044).

Programmer 104 may output an indication of whether the first stimulation and medication combination or the second stimulation and medication combination is more effective. For example, programmer 104 may output an indication of one or more of first time 1020, second time 1022, third time 1024, duration 1012 for the first stimulation and medication combination and one or more of first time 1020, second time 1042, third time 1044, duration 1040 for the second stimu-lation and medication combination. For instance, program-mer 104 may output an indication of the plot or a portion (e.g., LFP timeline segments) of the plot shown in FIG. 10. In some examples, programmer 104 may output an indica-tion of one or more of first time 1020, second time 1022, third time 1024, duration 1012 for the first stimulation and medication combination and one or more of first time 1020, second time 1042, third time 1044, duration 1040 for the second stimulation and medication combination to a remote device (e.g., a remote server or remote client).

In the example of FIG. 10, system 100 may determine the effectiveness of a combination of medication and stimula-tion. For instance, when patient 122 takes a first medication of the first stimulation and medication combination without stimulation, the LFP activity level of patient 102 reduces by 20% compared to no treatment. In this example, when system 100 applies a first stimulation of the first stimulation and medication combination to patient 122 without the first medication, the LFP activity level of patient 102 reduces by 30% compared to no treatment. However, configuring sys-tem 100 to determine the effectiveness of a combination of medication and stimulation may help to identify instances where the combination of medication and stimulation has a synergistic effect. For example, the combination of medica-tion and stimulation may reduce the LFP activity level of patient 102 by 70%.

Figure 11:
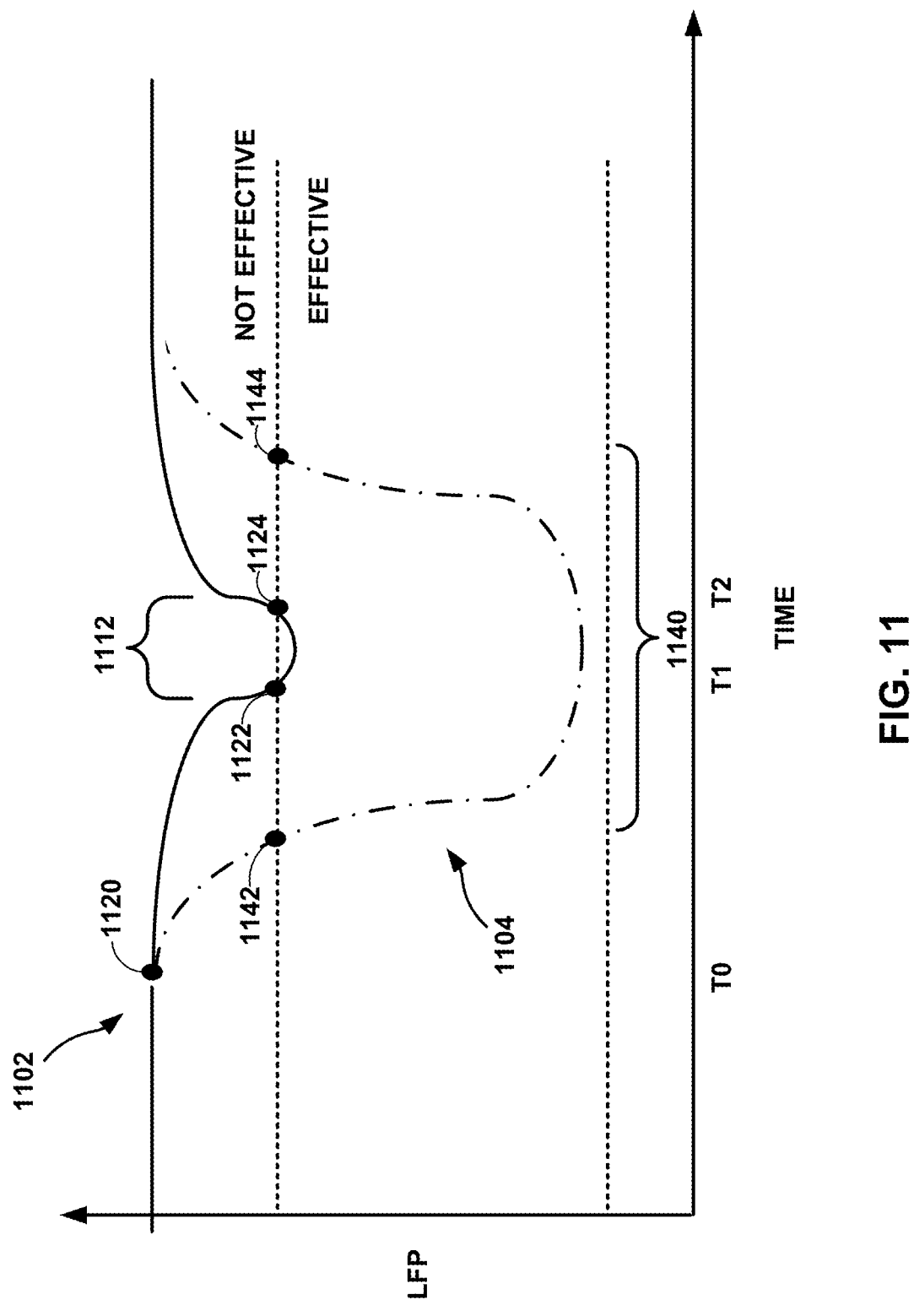
FIG. 11 is a plot illustrating an example of determining whether a current LFP response to a medication is better, worse, or the same as a baseline LFP response according to an example of the techniques of the disclosure.

FIG. 11 is a plot illustrating an example of determining whether a current LFP response to a medication is better, worse, or the same as a baseline LFP response according to an example of the techniques of the disclosure. The ordinate axis of FIG. 11 represents an LFP activity level 1102 of patient 122 for a medication and a baseline LFP activity level 1104 of patient 122 and the abscissa axis of FIG. 11 represents time. In the example of FIG. 11, patient 122 may take the medication at an initial time 1120 ("T0"). In the example of FIG. 11 during a different time period (e.g., a different day), patient 122 may take a baseline medication (e.g., the medication or a different medication) at an initial time 1120, which is overlayed with LFP activity level 1102 in FIG. 11 for illustrative purposes.

Similar to FIG. 8, system 100 may determine a second time 1122 for when the medication is effective, a third time 1124 for when the medication is no longer effective, and a duration 1112 indicating when the medication was effective. In this example, system 100 may determine a second time 1142 for when the baseline medication is effective, a third time 1144 for when the baseline medication is no longer effective, and a duration 1140 indicating when the baseline medication was effective.

In some examples, baseline LFP 1104 may represent a best or previous best medication (single medication or multiple medications). System 100 may compare duration 1112 of when the medication is effective to baseline duration 1140 for the medication. For example, LFP activity level 1102 may be determined when patient 102 has taken the baseline medication at first time 1102. That is, the baseline medication may not be as effective for patient 102 as determined when generating baseline LFP activity 1104. In another example, LFP activity level 1102 may be determined when patient 102 has taken a modified medication at first time 1102 that is different from the baseline medication. That is, the baseline medication may be more effective than the modified medication. System 100 could utilize a timeline view to display one or more medications overlayed on baseline LFP 1104 (and on each other) to allow the user to see the impact of the medication changes. The healthcare provider may denote the new medication/time/date that the medication was implemented. In this way, system 100 can determine when the medications were changed/implemented and overlay LFP timeline segments (e.g., first LFP activity level 1102 and second LFP activity level 1104).

In some examples, baseline LFP 1104 may represent an expected response to medication (single medication or multiple medications). System 100 may compare duration 1112 of when the medication is effective to baseline duration 1140 for the medication. For example, LFP activity level 1102 may be a most recent measurement from IMD 106. That is, a patient may be prescribed to take medication every four hours (e.g., at 8:00, 12:00, 16:00, 20:00, 24:00). In this example, system 100 may determine that patient 122 may have missed a dose of medication and/or took an incorrect dosage of the medication in response to duration 1140 being greater than duration 1112 by more than a threshold. In response to a determination that patient 122 may have missed a dose of medication and/or took an incorrect dosage of the medication, system 100 may output a reminder to patient 122 to take the medication.

Figure 12:
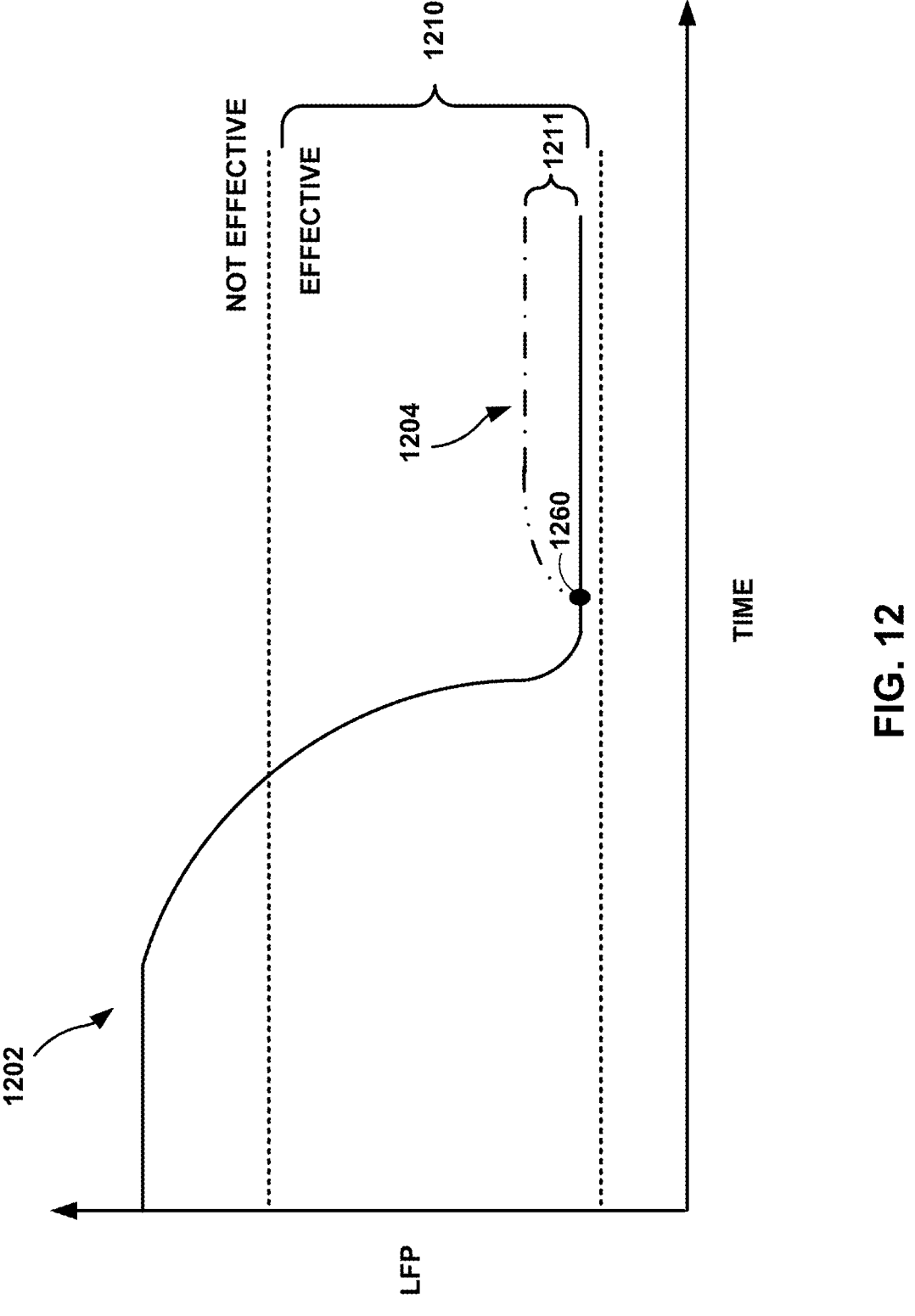
FIG. 12 is a plot illustrating an example of changing a stimulation based on an LFP response according to an example of the techniques of the disclosure.

FIG. 12 is a plot illustrating an example of changing a stimulation based on an LFP response according to an example of the techniques of the disclosure. The ordinate axis of FIG. 12 represents an LFP activity level 1202 of patient 122 for a treatment (e.g., medication or both stimulation and medication) and a titrated LFP activity level 1204 of patient 122 and the abscissa axis of FIG. 12 represents time.

Knowing the effectiveness of the medications alone, stimulation alone, and/or both medication(s) and stimulation may help the user better titrate the medication, stimulation values, and/or threshold values. Given this information, system 100 could provide guidance of stimulation changes to help optimize the therapy and/or outcome. System 100 may modify a stimulation for patient 122 based on LFP activity level 1202 of patient 122. For example, if LFPs are dropped to a therapeutic range and stay there consistently, system 100 could attempt to reduce the stimulation amplitude slightly to see if the LFP changes. For example, if LFP activity level 1202 is within range of LFP values 1210, system 100 could attempt to reduce the stimulation amplitude slightly, which in the example of FIG. 12 results in titrated LFP activity level 1204. In some examples, system 100 may attempt to reduce the stimulation amplitude based on a patient reported outcome. For instance, system 100 may refrain from attempting to reduce the stimulation amplitude when patient 122 indicates to refrain from titrating the stimulation to reduce a battery consumption of IMD 106.

If the LFP does not change or changes less than a threshold amount, system 100 may reduce the stimulation amplitude a little more until the LFP begins to slightly rise or rise more than the threshold amount. For example, if change 1211 is less than a threshold amount, system 100 could further reduce the stimulation amplitude. In this example, system 100 may raise the stimulation back to where the LFP used the lowest stimulation amplitude while having no LFP changes or LFP changes that are less than the threshold amount. For example, system 100 may raise the stimulation, which in the example of FIG. 12 results in titrated LFP activity level 1204. In this way, system 100 may help to maximize battery longevity while potentially keeping symptom therapy outcomes for patient 102 the same as using the higher stimulation amplitude.

While in the above examples, system 100 modified a stimulation for patient 122 based on LFP activity level 1202 of patient 122, in some examples, system 100 may additionally or alternatively modify the stimulation for patient 122 based on a duration of when the medication is effective.

In some examples, system 100 may be configured to receive an input, also referred to herein as feedback, from a user (e.g., patient 122 or a caretaker) through a device, such as programmer 104, or other accessory. System 100 may use the input from the user to help determine the efficacy of medication and/or stimulation changes. Examples of the input from the user may include, for example, an indication of whether patient 122 feels good or has symptoms. System 100 may initiate the feedback. For example, system 100 could prompt or ask patient 122 for feedback on how they are doing. For instance, the feedback could either confirm, or clarify, changes that have been made. In this example, system 100 can incorporate the data (e.g., the feedback) along with the LFP activity level to the healthcare provider. In some examples, patient 122 could enter data as they see fit that would help provide other subjective data for system 100 to compile that would be shown to the healthcare provider.

Figure 13:
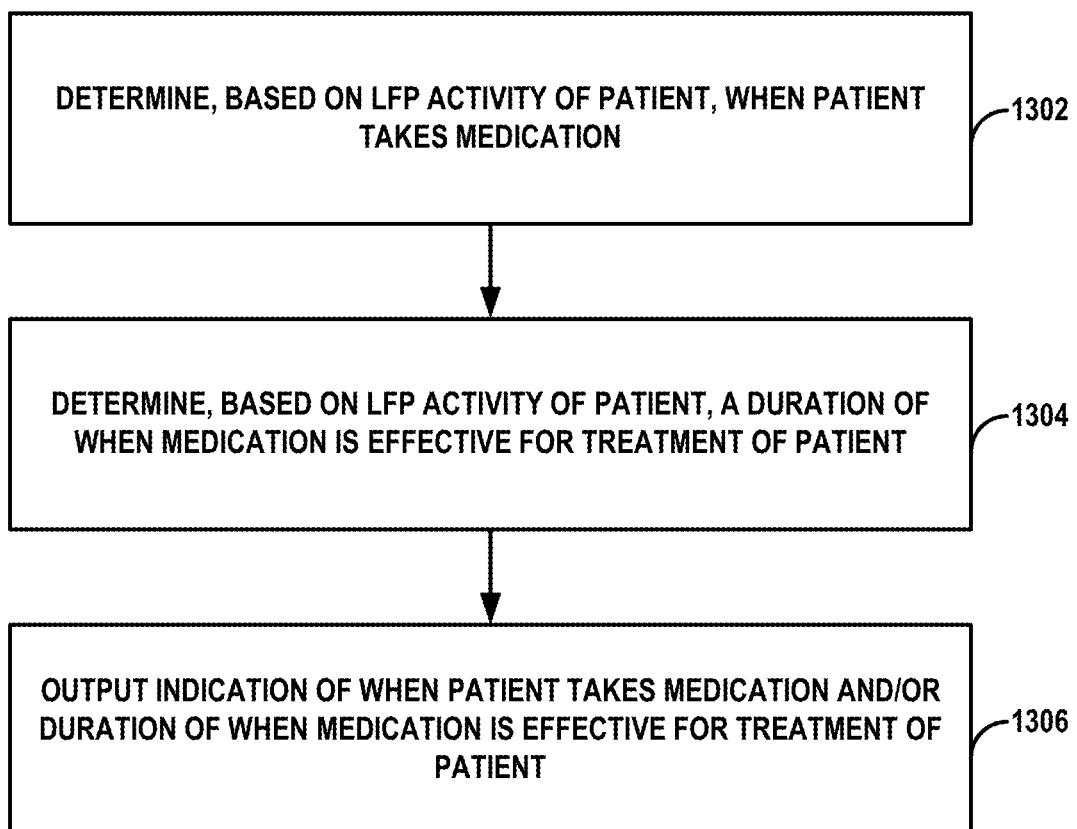
FIG. 13 is a flowchart illustrating an example operation for determining when the patient takes the medication and the duration of when the medication is effective for treatment of the patient in accordance with techniques of the disclosure.

FIG. 13 is a flowchart illustrating an example operation for determining when the patient takes the medication and the duration of when the medication is effective for treatment of the patient in accordance with techniques of the disclosure. In the example of FIG. 13, programmer 104 may determine when a patient takes medication and when the medication is effective, however, any combination of IMD 106, programmer 104, and one or more client devices (e.g., remote server 570 and/or remote client 572) may perform the process illustrated in FIG. 8. In some examples, the one or more processors may include IMD 106, which may be configured to apply electrical stimulation therapy to patient 122.

In the example of FIG. 13, programmer 104 may determine, based on LFP activity of the patient, when a patient takes medication (1302). Programmer 104 may determine, based on the LFP activity of the patient, a duration of when the medication is effective (1304). For example, programmer 104 may perform one or more steps illustrated in FIG. 14. In some examples, programmer 104 may skip step 1302 or step 1304. For instance, programmer 104 may receive an indication of when the patient takes the medication.

Programmer 104 may output an indication of when the patient takes the medication and/or the duration of when the medication is effective to facilitate a treatment for the patient (1306). For example, programmer 104 may display the indication of when patient 122 takes the medication and/or the duration of when the medication is effective to facilitate a treatment for the patient on a display of programmer 104. In some examples, programmer 104 may output the indication of when patient 122 takes the medication and/or the duration of when the medication is effective to facilitate a treatment for the patient to a remote device.

FIG. 14 is a flowchart illustrating an example operation for determining the duration of when the medication is effective for treatment of the patient based on a range of LFP values in accordance with techniques of the disclosure. In the example of FIG. 14, programmer 104 may determine when a patient takes medication and when the medication is effective, however, any combination of IMD 106, programmer 104, and one or more client devices (e.g., remote server 570 and/or remote client 572) may perform the process illustrated in FIG. 14. In some examples, the one or more processors may include IMD 106, which may be configured to apply electrical stimulation therapy to patient 122.

In the example of FIG. 14, programmer 104 may receive an indication of a range of LFP values for determine whether medication is effective for treatment of a patient (1402). For instance, programmer 104 may receive the indication of the range of LFP values from a remote device (e.g., from a clinician using the remote device). Programmer 104 may determine, based on the LFP activity of patient 122 and after patient 122 takes the medication, when the medication is effective for treatment of patient 122 (1404). For example, programmer 104 may determine when the medication is effective for treatment of patient 122 to be when a magnitude of the LFP activity of the patient satisfies (e.g., is within) the range of LFP values.

Programmer 104 may determine, based on the LFP activity of patient 122 and after the determination that medication is effective for treatment of patient 122, when the medication is not effective for treatment of patient 122 (1406). For example, programmer 104 may determine when the medication is not effective for treatment of patient 122 to be when a magnitude of the LFP activity of the patient does not satisfy (e.g., is not within or is outside) the range of LFP values.

Programmer 104 may determine the duration of when the medication is effective based on when the medication is effective for treatment of the patient and when the medication is not effective for treatment of the patient (1408). For example, programmer 104 may determine a difference in the time between when the medication is effective for treatment and when the medication was not effective for treatment of patient 122.

In some examples, programmer 104 may output an instruction to request a user input to confirm that the medication is not currently effective for treatment of patient 122 in response to determining that the medication is not effective for treatment of patient 122. In this example, programmer 104 may determine whether a user input responsive to the request indicates that the medication is not effective for treatment of the patient. Programmer 104 may store an indication of whether a user input responsive to the request indicates that the medication is not effective for treatment of patient 122 and an indication of the LFP activity of patient 122 during the duration of when the medication is effective.

In some examples, programmer 104 may determine, based on the LFP activity of the patient and after the patient takes the medication, that the patient is overmedicated by the medication. For example, programmer 104 may determine that the LFP activity is less than the range of LFP values. In this example, programmer 104 may output an indication that the patient is overmedicated by the medication in response to determining that the patient is overmedicated. For example, programmer 104 may display the indication that the patient is overmedicated by the medication on a display of programmer 104. In some examples, programmer 104 may output the indication that the patient is overmedicated by the medication to a remote device.

Other illustrative examples of the disclosure are described below.

Example 1. A method for determining an efficacy of medication treatment for a patient, the method comprising: determining, by one or more processors, based on a local field potential (LFP) activity of the patient, when the patient takes medication and/or a duration of when the medication is effective; and outputting, by the one or more processors, an indication of when the patient takes the medication and/or the duration of when the medication is effective to facilitate a treatment for the patient.

Example 2. The method of example 1, wherein determining the duration of when the medication is effective comprises: determining, based on the LFP activity of the patient and after the patient takes the medication, when the medication is effective for treatment of the patient; determining, based on the LFP activity of the patient and after the medication is effective for treatment of the patient, when the medication is not effective for treatment of the patient; and determining the duration of when the medication is effective based on when the medication is effective for treatment of the patient and when the medication is not effective for treatment of the patient.

Example 3. The method of example 2, further comprising: outputting, by the one or more processors, an instruction to request a user input to confirm that the medication is not currently effective for treatment of the patient in response to determining that the medication is not effective for treatment of the patient; determining, by the one or more processors, whether the user input responsive to the request indicates that the medication is not effective for treatment of the patient; and storing, by the one or more processors, an indication of whether the user input responsive to the request indicates that the medication is not effective for treatment of the patient and an indication of the LFP activity of the patient during the duration of when the medication is effective.

Example 4. The method of any of examples 2-3, wherein determining when the medication is effective for treatment of the patient comprises determining that a magnitude of the LFP activity of the patient satisfies a range of LFP values.

Example 5. The method of example 4, wherein determining that the magnitude of the LFP activity of the patient satisfies the range of LFP values comprises determining that the magnitude of the LFP activity of the patient is within the range of LFP values.

Example 6. The method of example 4, wherein determining when the medication is not effective for treatment of the patient comprises determining that the magnitude of the LFP activity of the patient does not satisfy the range of LFP values.

Example 7. The method of example 6, wherein determining that the magnitude of the LFP activity of the patient does not satisfy the range of LFP values comprises determining that the magnitude of the LFP activity of the patient is outside of the range of LFP values.

Example 8. The method of any of examples 1-7, further comprising receiving, by the one or more processors, an indication of the range of LFP values.

Example 9. The method of any of examples 1-8, further comprising receiving, by the one or more processors, an indication of when the patient takes the medication.

Example 10. The method of any of examples 1-8, further comprising determining, by the one or more processors, when the patient takes the medication based on the LFP activity of the patient.

Example 11. The method of any of examples 1-10, further comprising: determining, by the one or more processors, based on the LFP activity of the patient and after the patient takes the medication, that the patient is overmedicated by the medication; and outputting, by the one or more processors, an indication that the patient is overmedicated by the medication in response to determining that the patient is over-medicated.

Example 12. The method of any of examples 1-11, further comprising: sensing, by the one or more processors, one or more bioelectric signals of brain of the patient, wherein the one or more bioelectric signals comprise the LFP activity of the patient; and applying, by the one or more processors, electrical stimulation therapy based on the one or more bioelectric signals of the brain of the patient.

Example 13. A system for providing stimulation to a patient, the system comprising: sensing circuitry configured to generate a local field potential (LFP) activity of a patient; and processing circuitry configured to: determine, based on the LFP activity of the patient, when the patient takes medication and/or a duration of when the medication is effective; and output an indication of when the patient takes the medication and/or the duration of when the medication is effective to facilitate a treatment for the patient.

Example 14. The system of example 13, wherein the medical device is configured to perform the method of any combination of examples 2-12.

Example 15. The system of any of examples 13-13, further comprising an implantable medical device comprising the sensing circuitry.

Example 16. The system of any of examples 13-15, further comprising an external programmer comprising the processing circuitry.

Example 17. A computer-readable storage medium having stored thereon instructions that, when executed, cause processing circuitry to perform the method of any of examples 1-12.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method for determining an efficacy of medication treatment for a patient, the method comprising:
   generating, by one or more processors and based on processing one or more bioelectric signals sensed from the patient, an indication of a local field potential (LFP) activity of the patient;
   determining, by the one or more processors, at least one of:
      when the patient takes medication based on a decrease of a magnitude of the LFP activity of the patient; or
      a duration of when the medication is effective based on a duration during which the magnitude of the LFP activity of the patient satisfies a range of LFP values; and
   outputting, by the one or more processors, at least one of an indication of when the patient takes the medication or the duration of when the medication is effective to facilitate a treatment for the patient.

2. The method of claim 1, wherein determining the duration of when the medication is effective comprises:
   determining, based on the LFP activity of the patient and after the patient takes the medication, when the medication is effective for treatment of the patient;
   determining, based on the LFP activity of the patient and after the medication is effective for treatment of the patient, when the medication is not effective for treatment of the patient; and
   determining the duration of when the medication is effective based on when the medication is effective for treatment of the patient and when the medication is not effective for treatment of the patient.

3. The method of claim 2, further comprising:

outputting, by the one or more processors, an instruction to request a user input to confirm that the medication is not currently effective for treatment of the patient in response to determining that the medication is not effective for treatment of the patient;

determining, by the one or more processors, whether the user input responsive to the request indicates that the medication is not effective for treatment of the patient; and storing, by the one or more processors, an indication of whether the user input responsive to the request indicates that the medication is not effective for treatment of the patient and an indication of the LFP activity of the patient during the duration of when the medication is effective.

4. The method of claim 1, wherein the duration during which the magnitude of the LFP activity of the patient satisfies the range of LFP values comprises a duration during which the magnitude of the LFP activity of the patient is within the range of LFP values.

5. The method of claim 1, further comprising determining when the medication is not effective for treatment of the patient based on determining that the magnitude of the LFP activity of the patient does not satisfy the range of LFP values.

6. The method of claim 5, wherein determining that the magnitude of the LFP activity of the patient does not satisfy the range of LFP values comprises determining that the magnitude of the LFP activity of the patient is outside of the range of LFP values.

7. The method of claim 1, further comprising receiving, by the one or more processors, an indication of the range of LFP values.

8. The method of claim 1, further comprising receiving, by the one or more processors, an indication of when the patient takes the medication.

9. The method of claim 1, further comprising:

determining, by the one or more processors, based on the LFP activity of the patient and after the patient takes the medication, that the patient is overmedicated by the medication; and outputting, by the one or more processors, an indication that the patient is overmedicated by the medication in response to determining that the patient is overmedicated.

10. The method of claim 1, further comprising:

sensing, by the one or more processors, the one or more bioelectric signals of brain of the patient, wherein the one or more bioelectric signals comprise the LFP activity of the patient; and applying, by the one or more processors, electrical stimulation therapy based on the one or more bioelectric signals of the brain of the patient.

11. The method of claim 1, further comprising determining, based on the LFP activity of the patient, whether the medication is more effective than another medication.

12. The method of claim 1, further comprising determining, based on the duration of when the medication is effective, whether the medication is more effective than another medication.

13. The method of claim 1, further comprising determining, based on the LFP activity of the patient, whether a combination of the medication and a first stimulation is more effective than another combination of a second medication and a second stimulation.

14. The method of claim 1, further comprising determining, based on the duration of when the medication is effective, whether a combination of the medication and a first stimulation is more effective than another combination of a second medication and a second stimulation.

15. The method of claim 1, further comprising comparing the duration of when the medication is effective to a baseline duration of when the medication is effective.

16. The method of claim 1, further comprising modifying a stimulation for the patient based on one or more of the LFP activity of the patient or the duration of when the medication is effective.

17. A system for providing stimulation to a patient, the system comprising:

sensing circuitry configured to sense one or more bioelectric signals from a patient; and processing circuitry configured to:

generate, based on processing the one or more bioelectric signals sensed from the patient, an indication of a local field potential (LFP) activity of the patient;

determine, based on the LFP activity of the patient, at least one of:

when the patient takes medication based on a decrease of a magnitude of the LFP activity of the patient; or a duration of when the medication is effective based on a duration during which the magnitude of the LFP activity of the patient satisfies a range of LFP values; and output at least one of an indication of when the patient takes the medication or the duration of when the medication is effective to facilitate a treatment for the patient.

18. A non-transitory computer-readable storage medium having stored thereon instructions that, when executed, cause processing circuitry to:

generate, based on processing one or more bioelectric signals sensed from a patient, an indication of a local field potential (LFP) activity of the patient;

determine, based on the LFP activity of the patient, at least one of:

when the patient takes medication based on a decrease of a magnitude of the LFP activity of the patient; or a duration of when the medication is effective based on a duration during which the magnitude of the LFP activity of the patient satisfies a range of LFP values; and output at least one of an indication of when the patient takes the medication or the duration of when the medication is effective to facilitate a treatment for the patient.

* * * * *